(12) United States Patent
Farnan

(10) Patent No.: US 9,028,393 B2
(45) Date of Patent: May 12, 2015

(54) COAXIAL BALLOON DELIVERY DEVICE AND METHOD OF DELIVERING A TRANSSEPTAL CANNULA TO A HEART

(71) Applicant: CircuLite, Inc., Teaneck, NJ (US)

(72) Inventor: Robert C. Farnan, Ridgewood, NJ (US)

(73) Assignee: CircuLite, Inc., Teaneck, NJ (US)

( * ) Notice: Subject to any disclaimer, the term of this patent is extended or adjusted under 35 U.S.C. 154(b) by 0 days.

(21) Appl. No.: 13/888,641

(22) Filed: May 7, 2013

(65) Prior Publication Data

US 2013/0231521 A1    Sep. 5, 2013

Related U.S. Application Data

(62) Division of application No. 12/720,012, filed on Mar. 9, 2010, now Pat. No. 8,460,168.

(60) Provisional application No. 61/163,926, filed on Mar. 27, 2009.

(51) Int. Cl.
  *A61M 25/10*   (2013.01)
  *A61M 1/10*    (2006.01)
  (Continued)

(52) U.S. Cl.
  CPC .............. *A61M 1/10* (2013.01); *A61M 1/101* (2013.01); *A61M 25/005* (2013.01); *A61M 25/0069* (2013.01); *A61M 25/0074* (2013.01); *A61M 25/0082* (2013.01); *A61M 25/0097* (2013.01); *A61M 25/0194* (2013.01); *A61M 25/04* (2013.01); *A61M 25/1006* (2013.01); *A61M 25/1018* (2013.01); *A61M 27/00* (2013.01);

(Continued)

(58) Field of Classification Search
  CPC ................. A61M 25/1018; A61M 1/1072
  USPC .......................................... 600/16
  See application file for complete search history.

(56) References Cited

U.S. PATENT DOCUMENTS

| 5,658,309 A | 8/1997 | Berthiaume et al. | |
| 5,695,479 A * | 12/1997 | Jagpal | 604/264 |
| 2003/0199914 A1 * | 10/2003 | Diaz | 606/194 |

FOREIGN PATENT DOCUMENTS

| JP | H11503646 A | 3/1999 |
| WO | 9632882 A1 | 10/1996 |

OTHER PUBLICATIONS

Japanese Patent Office, Notice of Reasons for Rejection in JP Application No. 2010-072468, Feb. 3, 2014.

*Primary Examiner* — Eric D. Bertram
(74) *Attorney, Agent, or Firm* — Wood, Herron & Evans, L.L.P.

(57) ABSTRACT

A transseptal cannula having a flexible cannula body, a left atrial anchor coupled to the distal end of the flexible cannula body, and a right atrial anchor operable to be attached to the left atrial anchor in vivo. The left and right atrial anchors are implanted and deployed separately. Delivery of the transseptal cannula to a heart tissue can include a low profile coaxial balloon catheter comprising a tube body including an inner member and an outer member surrounding the inner member and thereby creating an inflation channel between the inner and outer members, a hub coupled to the proximal portion of the tube body and including a fluid space in fluid communication with the inflation channel; and a balloon coupled to the distal portion of the tube body, wherein the balloon is in fluid communication with the inflation channel. The hub of the coaxial balloon catheter is constructed with a low profile so that other surgical devices can be directed over the coaxial hub without deflating and removing the balloon.

8 Claims, 20 Drawing Sheets

(51) Int. Cl.
*A61M 25/04* (2006.01)
*A61M 27/00* (2006.01)
*A61M 1/12* (2006.01)
*A61M 25/00* (2006.01)
*A61M 25/01* (2006.01)
*A61M 25/06* (2006.01)

(52) U.S. Cl.
CPC .................. *A61M 2025/0681* (2013.01); *A61M 2025/1061* (2013.01); *A61M 1/122* (2013.01)

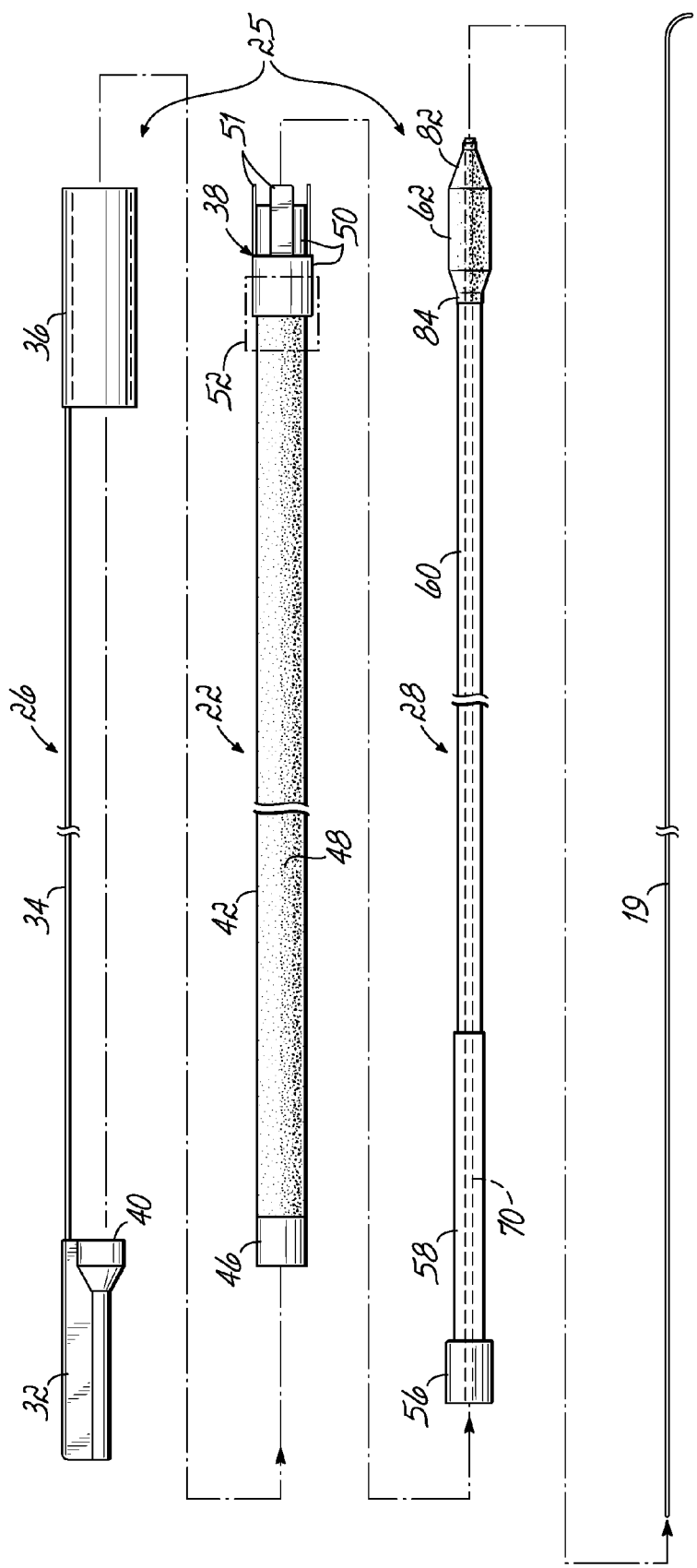
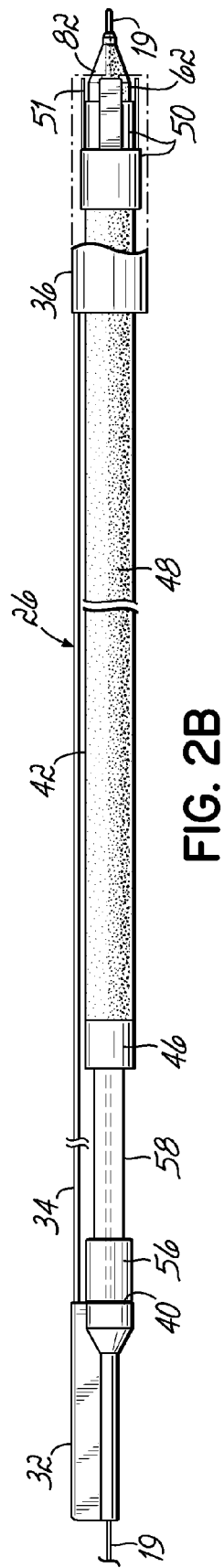
FIG. 2A
FIG. 2B

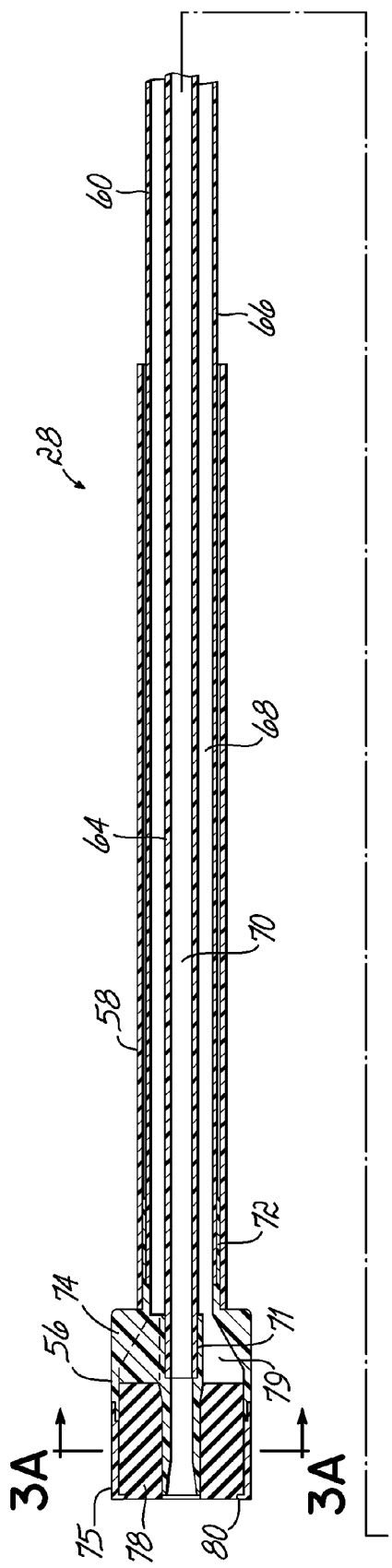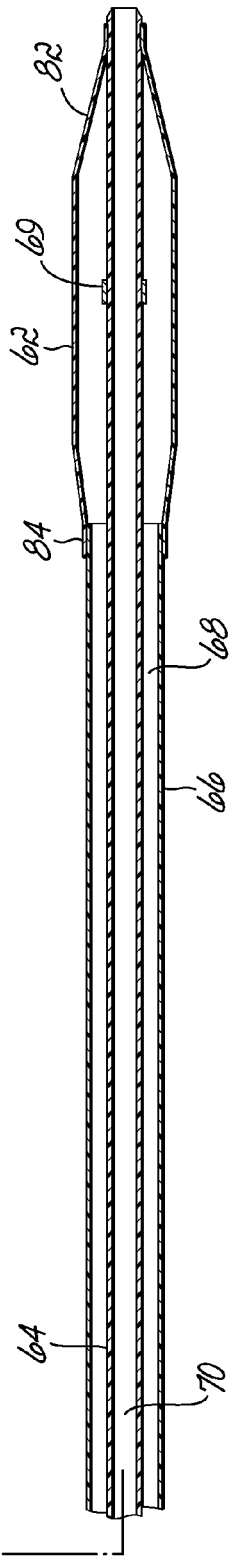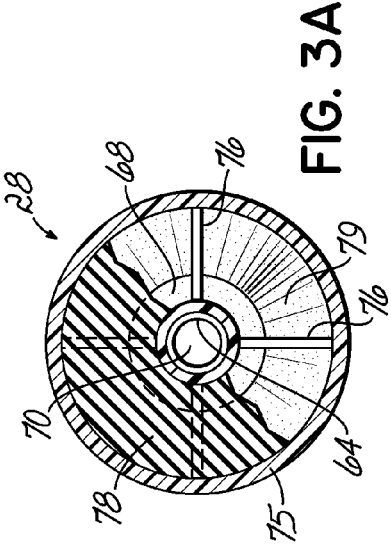
FIG. 3
FIG. 3A

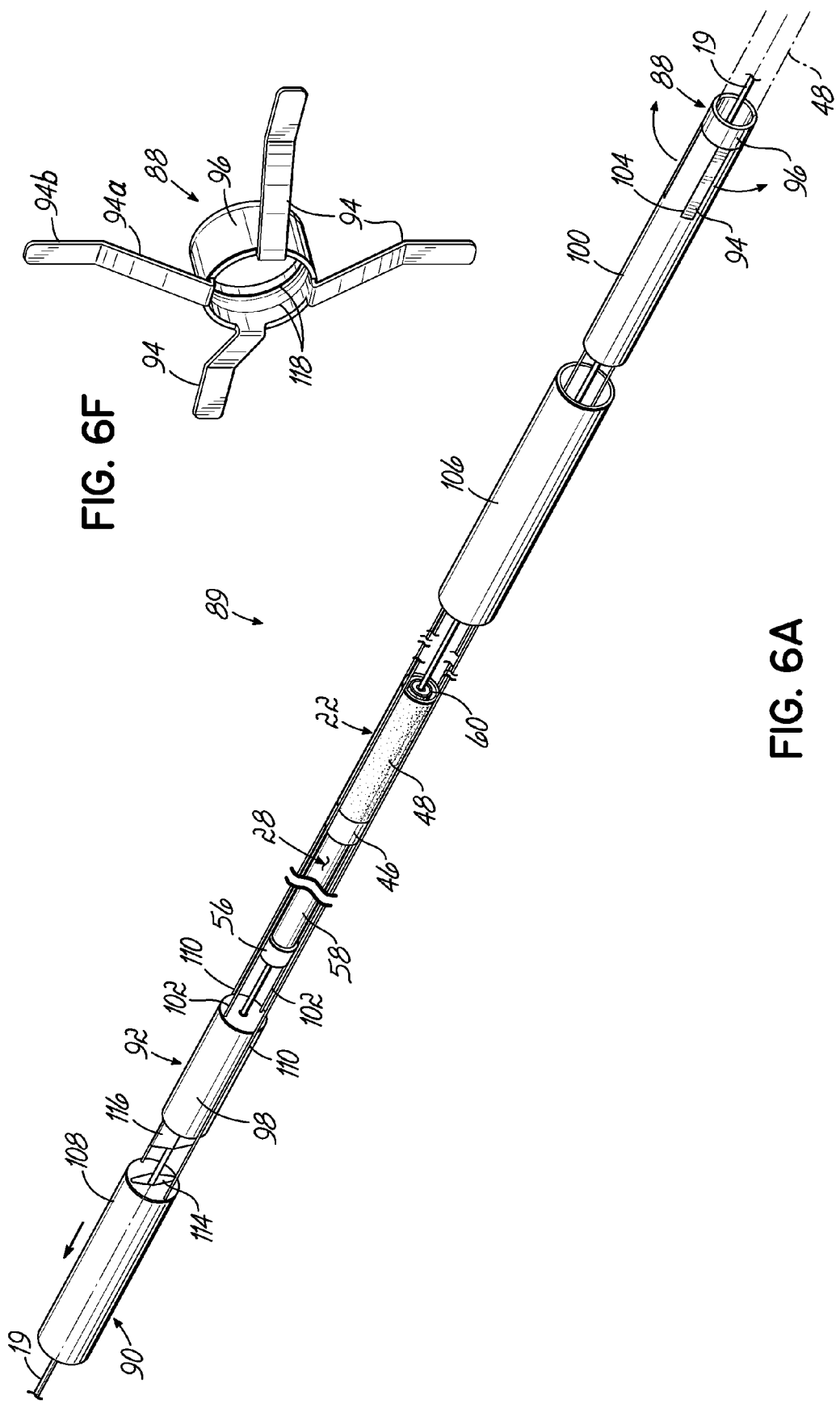

COAXIAL BALLOON DELIVERY DEVICE AND METHOD OF DELIVERING A TRANSSEPTAL CANNULA TO A HEART

CROSS-REFERENCE TO RELATED APPLICATION

This application is a divisional of U.S. application Ser. No. 12/720,012, filed Mar. 9, 2010 (now U.S. Pat. No. 8,460,168) which claims the benefit of U.S. Provisional Patent Application Ser. No. 61/163,926, filed on Mar. 27, 2009, the disclosures of which are incorporated by reference herein.

BACKGROUND

Circulatory assist devices were developed over a decade ago and provide assistance to a diseased heart by way of a mechanical pump. In this way, the circulation of blood through the vascular network is aided despite the presence of diseased tissue. Traditionally, these circulatory assist devices included an implantable pump, a controller (internal or external), and inflow and outflow tubes connecting the pump to the vascular network. The FDA has approved circulatory assist devices to partially relieve the symptoms of breathlessness and fatigue that are associated with severe heart failure and can drastically improve a patient's quality of life.

The surgical process associated with the circulatory assist device is highly invasive. At the very least, the procedure involves a thoracotomy, i.e., the opening of the thoracic cavity between successive ribs to expose the internal organs. More typical is cardiac surgery, generally known as open-heart surgery, where the sternum is cut and split to expose the internal organs. Once the thoracic cavity is accessed, the physician must enter the pleural space and puncture both the pericardium and the myocardial wall. There are great risks and an extensive recovery time associated with the implantation surgery. As such, the patients with severe symptoms are not healthy enough for the surgical procedure.

A transseptal cannula is described in U.S. patent application Ser. No. 12/256,911, the disclosure of which is incorporated herein by reference in its entirety. The transseptal cannula described therein provides greater accessibility to the circulatory assist device by minimizing the invasiveness of the implantation surgery for those patients that would gain the most benefit while awaiting a heart transplant.

There continues to be a need to implement additional features that would facilitate the delivery of the transseptal cannula and/or that would allow the physician to maintain control over the transseptal cannula device during the surgical procedure.

SUMMARY

In one embodiment, a coaxial balloon catheter is provided and includes a tube body, a coaxial hub, and a balloon. The tube body includes an inner member and outer member surrounding the inner member and thereby creating an inflation channel between the inner and outer members. The hub is coupled in a coaxial manner to the proximal portion of the tube body and includes a fluid space in fluid communication with the inflation channel. The coaxial hub has a low profile so that a surgical device can be loaded over the coaxial hub. The balloon is coupled to a distal portion of the tube body and a distal portion of the inner member extends through the balloon thereby creating an annular cavity between a wall of the balloon and the inner member.

A transseptal cannula assembly is also provided and includes a flexible cannula body, a left atrial anchor, and a right atrial anchor. The flexible cannula body includes distal and proximal ends with a lumen extending therebetween. The left atrial anchor is coupled to the distal end of the flexible cannula body and is configured to be deployed from a contracted state to an expanded state to engage at least one side of heart tissue is the expanded state. The right atrial anchor is attachable to the left atrial anchor in vivo and is configured to be deployed from a contracted state to an expanded state to engage an opposing side of the heart tissue in expanded state. The transseptal cannula may be used in combination with a left anchor delivery system including a sheath and a proximal hub. The transseptal cannula assembly may also be used in combination with a right anchor delivery system. The right anchor delivery system comprises a right anchor delivery apparatus configured to engage the left atrial anchor and couple the right atrial anchor to the left atrial anchor. A right anchor sheath includes a proximal hub and a sheath body configured to receive the right anchor delivery apparatus and move relative thereto for deploying the right atrial anchor into the expanded state.

Methods of delivering a transseptal cannula assembly to a heart tissue are also disclosed.

Various other details, embodiments and features are disclosed herein and are detailed below in conjunction with the accompanying drawings.

BRIEF DESCRIPTION OF THE FIGURES

FIG. 2A is a disassembled, side elevational view of a delivery apparatus and transseptal cannula assembly.

FIG. 2B is an assembled, side elevational view of the delivery apparatus with the transseptal cannula assembly.

FIG. 3 is a side elevational view of a coaxial balloon catheter, shown in cross-section.

FIG. 3A is a cross-sectional view of a coaxial hub of the coaxial balloon catheter, taken along line 3A-3A of FIG. 3.

FIG. 6A is a perspective view of an exemplary method of assembling the right anchor delivery system and back-loading the right anchor delivery system over the transseptal cannula assembly.

FIG. 6F is perspective view of the right atrial anchor.

DETAILED DESCRIPTION

Figure 1:
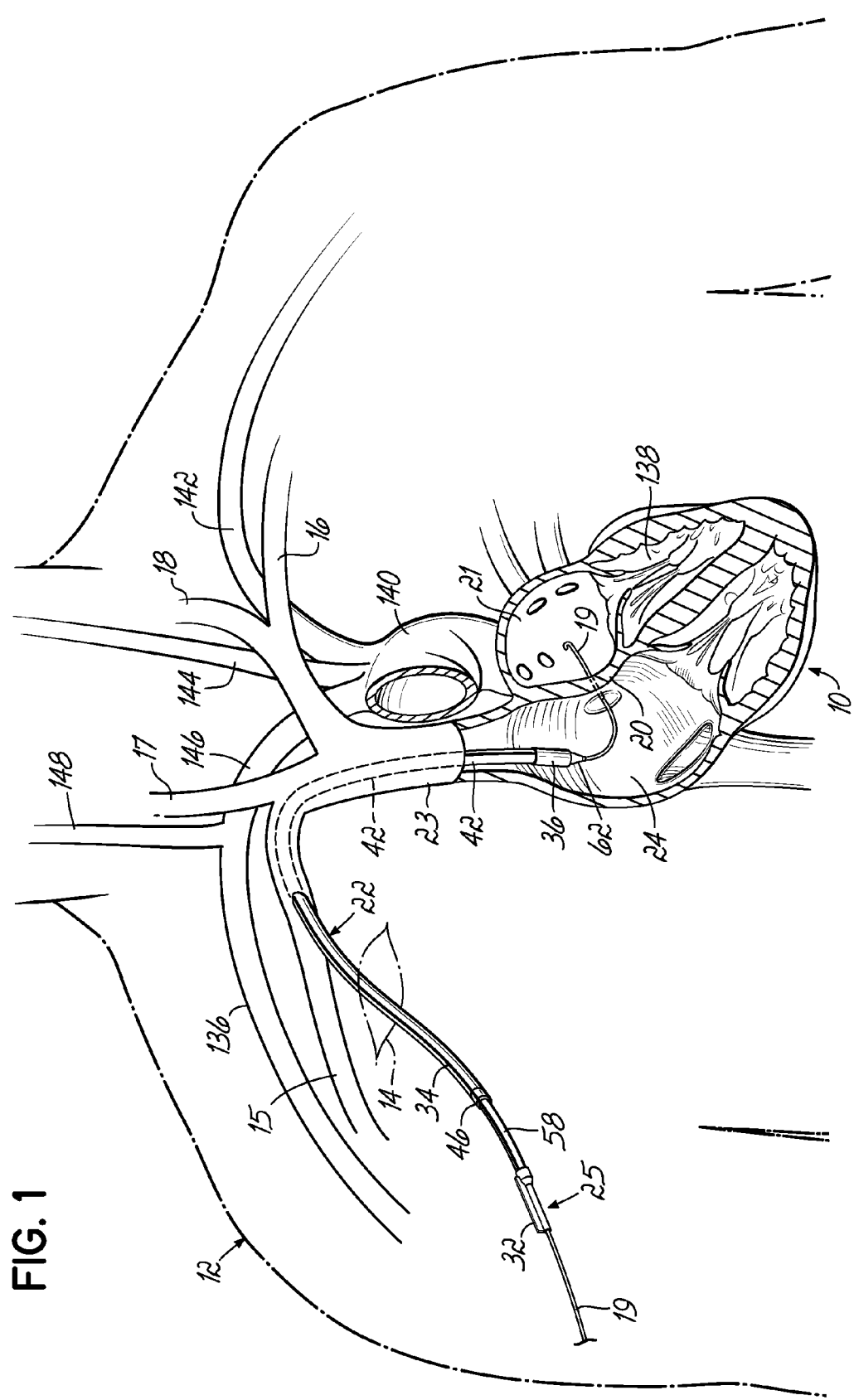
FIG. 1 is a diagrammatic view of an exemplary method of implanting the transseptal cannula assembly in a human heart, shown in cross-section.

Implanting a circulatory assist device according to one embodiment can begin with a percutaneous transseptal crossing procedure. FIG. 1 illustrates a portion of this procedure, where the physician gains access to the heart 10 of the patient 12 from a superior incision site 14. A suitable location for the superior incision site 14 can be substantially near a superior superficial vein, such as the right or left subclavian veins 15, 16; the right or left jugular veins 17, 18; or the junction between a jugular vein 17, 18 and the corresponding adjoining subclavian vein 15, 16. There are several methods by which the physician can gain access to the heart 10. One example not specifically illustrated here, but disclosed in U.S. patent application Ser. No. 12/256,911, the disclosure of which is incorporated herein by reference in its entirety, includes creating a femoral vein access site and directing an anchoring guide-element from the femoral vein access site to the patient's heart 10 and through a heart tissue. A distal portion of the anchoring guide-element is secured to the heart tissue while a proximal portion of the anchoring guide-element is transferred from the femoral vein access site to the superior superficial vein site via a capture device, such as a conventional snare device. Another example not specifically illustrated but also disclosed in U.S. patent application Ser. No. 12/256,911 includes directing a steerable guidewire from the superior superficial vein site directly to the patient's heart 10. The steerable guidewire then crosses the heart tissue.

Referring still to FIG. 1, once the guidewire 19 (or anchoring guide-element) traverses the heart tissue, such as the intra-atrial septum 20, and enters the left atrium 21, a transseptal cannula 22 with a left anchor delivery system 25 are back-loaded over a proximal end of the guidewire 19. The transseptal cannula 22 is then directed through the right subclavian vein 15, the superior vena cava 23, and into the right atrium 24.

FIG. 2A illustrates the details of the left anchor delivery system, which includes a delivery apparatus 26 and a coaxial balloon catheter 28 for aiding in implanting of the transseptal cannula 22. The delivery apparatus 26 has a proximal hub 32 and a sheath that is configured to receive and move relative to the flexible cannula body. The sheath, as illustrated, includes a distal sleeve 36 that is connected to the proximal hub 32 by at least one connector member 34. The proximal hub 32 provides visual and tactile feedback with respect to the deployment of a left atrial anchor 38 (described in detail below) of the transseptal cannula 22. The proximal hub 32 can be molded as a single polymeric material that is noncompliant, i.e., does not change shape during the physician's use. The proximal hub 32 of the delivery apparatus 26 may include a docking portion 40 for receiving a proximal end of the coaxial balloon catheter 28. The docking portion 40 sets a relative position between the coaxial balloon catheter 28 and the delivery apparatus 26 to aid in maintaining the left atrial anchor 38 within the distal sleeve 36 during the implanting procedure. The docking portion 40 may also aid in minimizing blood loss from between the guidewire 19 and the coaxial balloon catheter 28.

The at least one connector member 34 of the delivery apparatus 26 that couples the distal sleeve 36 to the proximal hub 32 and can be constructed from a rigid polymeric material or a metallic wire. While only one connector member 34 is shown, it would be understood that additional connector members 34 can be used. The connector members 34 allow the physician to maintain direct control of the transseptal cannula 22 while manipulating the delivery apparatus 26.

The distal sleeve 36 secures the left atrial anchor 38 during the delivery of the transseptal cannula 22 to the intra-atrial septum 20 (FIG. 1). The distal sleeve 36 can be constructed as single or multiple polymeric layers having lengths sufficient to cover the left atrial anchor 38.

In another embodiment not specifically illustrated, the sheath of the delivery apparatus extends from the proximal hub and for the length of the transseptal cannula to secure the left atrial anchor 38 during the delivery of the transseptal cannula 22. This sheath embodiment of the delivery apparatus is directed over the transseptal cannula 22 and moves relative thereto for deploying the left atrial anchor 38.

FIG. 2A illustrates the details of the transseptal cannula 22. The transseptal cannula 22 is designed such that left and right atrial anchors are implanted and deployed separately. This particular arrangement of the transseptal cannula is able to accommodate greater patient-to-patient variation in intra-atrial septal wall thicknesses and anatomies. The transseptal cannula includes a flexible cannula body 42 and the distally located left atrial anchor 38. The flexible cannula body 42 can be constructed of a polymeric material, such as thermoplastic or thermoset. A thin-film metallic coating may be applied to the polymeric material to inhibit the formation of a thrombosis. Other coatings can also be applied, such as with polyethylene terephthalate glycol (PETG) for lubricating the flexible cannula body 42. The flexible cannula body 42 may include both a pliable cannula portion 46 and a reinforced cannula portion 48. The pliable cannula portion 46 allows the flexible cannula body 42 to be secured to a circulatory assist device. The reinforced cannula portion 48 provides structural stability, increases the ease of manipulating the transseptal cannula 22 through the vascular network, and decreases the likelihood of the flexible cannula body 42 kinking within the vascular network. The reinforced cannula portion 48 may be constructed by single and/or multi-layer encapsulation of a wire braid or coil; the pliable cannula portion 46 may or may not include the wire braid or coil.

The left atrial anchor 38 includes a tip 50 and at least two opposed struts 51 coupled to the tip 50. When implanted, the tip 50 will create a shunt through the intra-atrial septum 20 (FIG. 1). The overall length of the tip 50 can vary according to a particular patient's anatomical needs. Accordingly, in some embodiments, the distal end of the tip 50 could extend as far as 1 cm into the left atrium 21 (FIG. 1); however, in other embodiments, the length of the tip 50 would be flush with the intra-atrial septum 20 (FIG. 1). The tip 50 can be constructed from a polished metallic, such as titanium (Ti), or from a polymeric material with tungsten (W) embedded for fluoroscopic localization.

The left atrial anchor 38 can, in some embodiments, include a cuff 52 (shown in phantom) to promote tissue in-growth and to further secure the transseptal cannula 22 to the heart tissue. The cuff may be any porous polymeric structure that provides an area for tissue in-growth, and increases the structural stability and sealing capacity as compared to the tip 50 alone. Suitable materials for the cuff 52 may include expanded polytetrafluoroethylene (ePTFE) and DACRON. The cuff 52 can generally be in at least one of two locations: an inner cuff 52 at the junction between the tip 50 and the flexible cannula body 42; or an outer cuff (not shown) surrounding a joint between the struts 51 and the tip 50. The outer cuff can provide the added benefit of minimizing a galvanic response between the tip 50 and the struts 51.

Referring still to FIG. 2A, but also to the assembled view in FIG. 2B, the delivery apparatus 26 and the transseptal cannula 22 are shown to coaxially surround the coaxial balloon catheter 28. The coaxial balloon catheter 28 has a coaxial hub 56, a strain relief 58, a tube body 60, and a balloon 62.

FIG. 3 illustrates the coaxial balloon catheter 28 with greater detail. The tube body 60 has an inner member 64, an outer member 66, and an inflation channel 68 therebetween. The inner and outer members 64, 66 can be tubular structures extending from the coaxial hub 56 to the balloon 62. The inner and outer members 64, 66 of the tube body 60 may be formed by an extrusion process from a flexible polymeric material, such as PEBAX or polyurethane. The inflation channel 68 provides a liquid conduit for an inflation fluid, such as saline or a contrast medium, to travel between the coaxial hub 56 and the balloon 62.

The proximal end of the inner member 64 is coupled to the coaxial hub 56 while the distal end of the inner member 64 extends through the balloon 62 and is coupled at the distal end of the balloon 62. The inner member 64 includes a lumen 70 that is substantially similar in diameter to the diameter of the guidewire 19 (FIG. 2A). The inner member 64 can also include at least one distally located marker 69 constructed from a metallic material, such as gold (Au) or platinum (Pt) or from a polymeric material embedded with a dense powder, such as tungsten (W). The marker 69 aids the physician in positioning the transseptal cannula 22 in vivo and in a manner that is described in detail below. Though not shown, if two or more marker bands are used, then the more distal marker band can be used to position the left atrial anchor 38 (FIG. 2A) within the left atrium 21 (FIG. 1) while the more proximal marker band can be used to position the right atrial anchor (discussed below) within the right atrium 24 (FIG. 1).

The proximal end of the outer member 66 of the coaxial balloon catheter 28 is coupled to the coaxial hub 56 while the distal end of the outer member 66 is coupled to the proximal end of the balloon 62. The hub-inner member bond 71 may be positioned proximal to the hub-outer member bond 72 to improve lumen inflation patency. A chemical bond (UV adhesive) or energy transfer process (thermal melting or RF) can be used to couple the inner and outer member 64, 66 to the coaxial hub 56.

FIGS. 3 and 3A illustrate the coaxial hub 56 of the coaxial balloon catheter 28. The coaxial hub 56 is constructed to have a low profile, such as a cylindrical or other straight or continuous outer profile, that would allow other hollow or tubular surgical devices to be directed over the coaxial hub 56 without deflating and removing the balloon 62. This is unlike a typical Y-shaped hub, for example, that would not allow such a function. The coaxial hub 56 has a hub-body 74, a hub-cap 75, a plurality of spokes 76, and a grommet 78. The hub-body 74 and hub-cap 75 form the main body of the coaxial hub 56. The plurality of spokes 76 are integrally molded within the hub-body 74, provide a positive stop for the grommet 78, and define a fluid space 79 that is in fluidic communication with the inflation channel 68. The plurality of spokes 76 can also provide a surface for coupling the inner member 64 to the coaxial hub 56. The grommet 78 provides a fluid-tight seal for holding a desired liquid pressure within the balloon 62 while permitting a syringe needle, or other similar solid object, to puncture and pass to the fluid space 79. The grommet 78 can be self-healing, i.e., maintains the fluid seal after the syringe needle has been removed. The hub-cap 75 can include a grommet retention feature 80 to prevent migration of the grommet 78 from the coaxial hub 56 after assembly.

The hub-body 74 and hub-cap 75 of the coaxial hub 56 can be molded from the same, or different, rigid materials that will resist compression. Suitable materials may include nylon or polycarbonate. The grommet 78 is formed by a molding process of an elastomeric material, such as polyurethane or silicone (Si). Once the grommet 78 is positioned within the hub-cap 75, the hub-cap 75 and hub-body 74 are bonded using chemical bonding (UV adhesives) or an energy transfer process (thermal melting or RF).

The strain relief 58 can be bonded to the coaxial hub 56 by interference fit or by chemical bond. The strain relief 58 strengthens the connection between the rigid coaxial hub 56 and the more flexible tube body 60 and provides a transition that aids in kink resistance at this location.

Continuing with FIG. 3, the balloon 62 can be constructed from a compliant polymeric material (lower durometer) for easy inflation or from a noncompliant polymeric material (higher durometer) that will resist change with increases in fluidic pressure. Suitable compliant materials can include PEBAX or polyurethane while noncompliant materials can include nylon or polyethylene terephthalate (PET). The balloon material is shaped to a cylindrical shape by a thermoforming process and is then bonded to the inner and outer members 64, 66 by either an energy transfer process (thermal melting or RF) or a chemical bonding (UV adhesive). The walls of the balloon 62 and the inner member 64 create an annular cavity 86 in fluid communication with the inflation channel 68 of the tube body 60. The fully inflated balloon 62 can withhold liquid pressures up to approximately 12 atm. The at least partially inflated balloon 62 will include a distal cone structure 82 that can facilitate the dilation of an opening through the intra-atrial septum 20 (FIG. 1) in a manner described below. The proximal end 84 of the balloon 62 should include sufficient surface area for coupling the balloon 62 to the outer member 66 by an energy transfer process or chemical bonding.

To inflate the balloon 62, the physician inserts a syringe needle of a syringe containing the inflation fluid through the grommet 78 of the coaxial hub 56 and into the fluid space 79. The inflation fluid is transferred from the syringe to the fluid space 79, the inflation channel 68, and into the annular cavity 86 of the balloon 62 where it will increase the fluid pressure and cause the walls of the balloon 62 to expand.

Figure 4A:
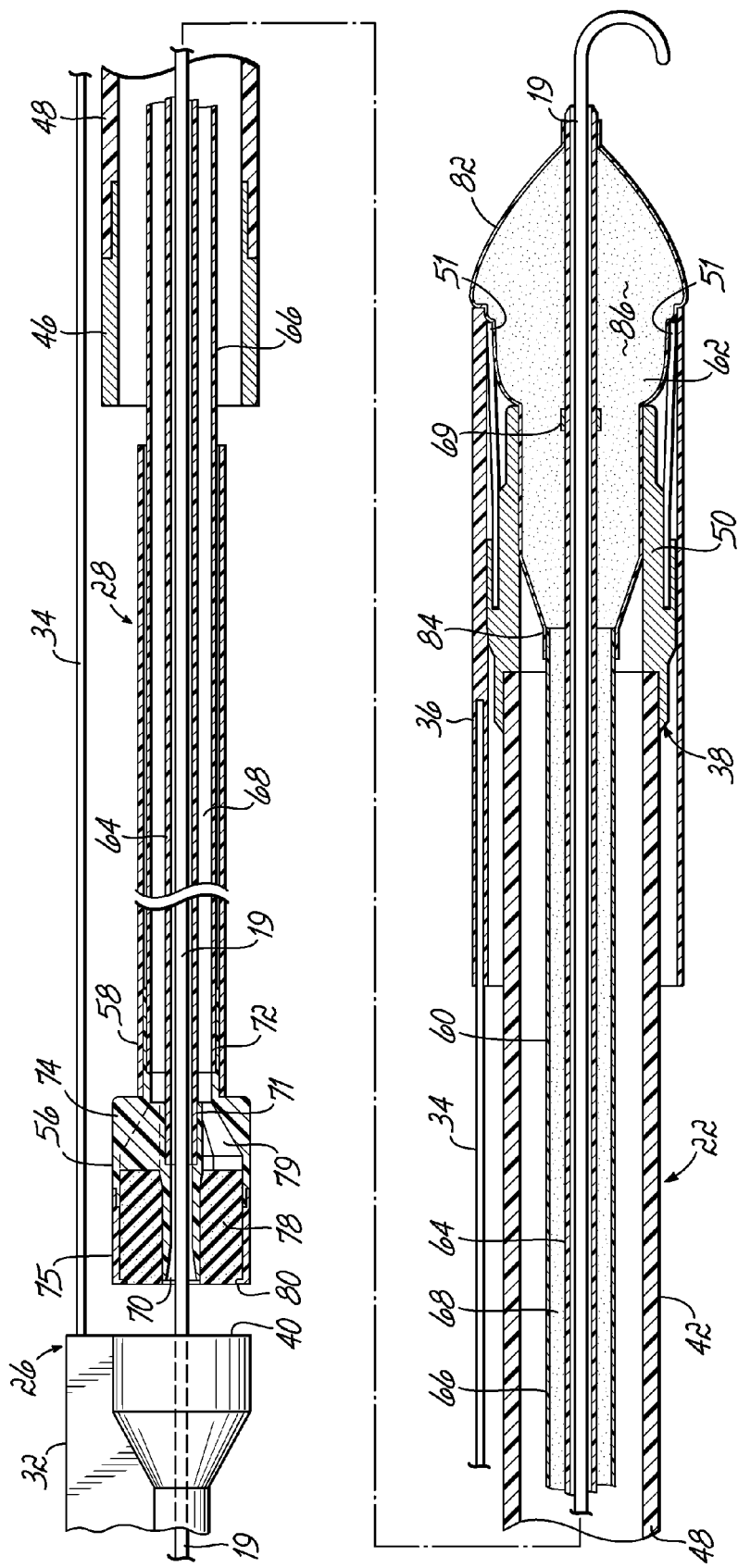
FIGS. 4A-4E are side elevational views in partial cross section of an exemplary method of deploying a left atrial anchor of the transseptal cannula assembly.

With the details of the left anchor delivery system 25 (FIG. 2A) and the transseptal cannula 22 described with some detail, the method of implanting the transseptal cannula 22 with the left atrial anchor 38 can continue with reference to FIGS. 4A-4F. FIG. 4A illustrates the delivery apparatus 26, the transseptal cannula 22, and the coaxial balloon catheter 28 coaxially loaded over the guidewire 19. The balloon 62 is positioned within the lumen of the tip 50 such that the marker 69 is approximately aligned with the distal end of the tip 50. Then, as the balloon 62 is inflated with the inflation fluid, the balloon 62 contacts the inner diameter of the tip 50. This contact between the tip 50 and the balloon 62 allows the physician to advance the transseptal cannula 22 and the coaxial balloon catheter 28 as a unit over the guidewire 19.

Also, as shown, the balloon 62 can be further inflated to contact the inner diameter of the distal sleeve 36 of the delivery apparatus 26. This contact between the distal sleeve 36 and the balloon 62 would further allow the physician to advance the transseptal cannula 22, the coaxial balloon catheter 28, and the delivery apparatus 26 as a unit over the guidewire 19. The relative positions of the coaxial balloon catheter 28 and the delivery apparatus 26 can further be aided by positioning the coaxial hub 56 of the coaxial balloon catheter 28 within the docking portion 40 of the delivery apparatus 26.

Figure 4B:
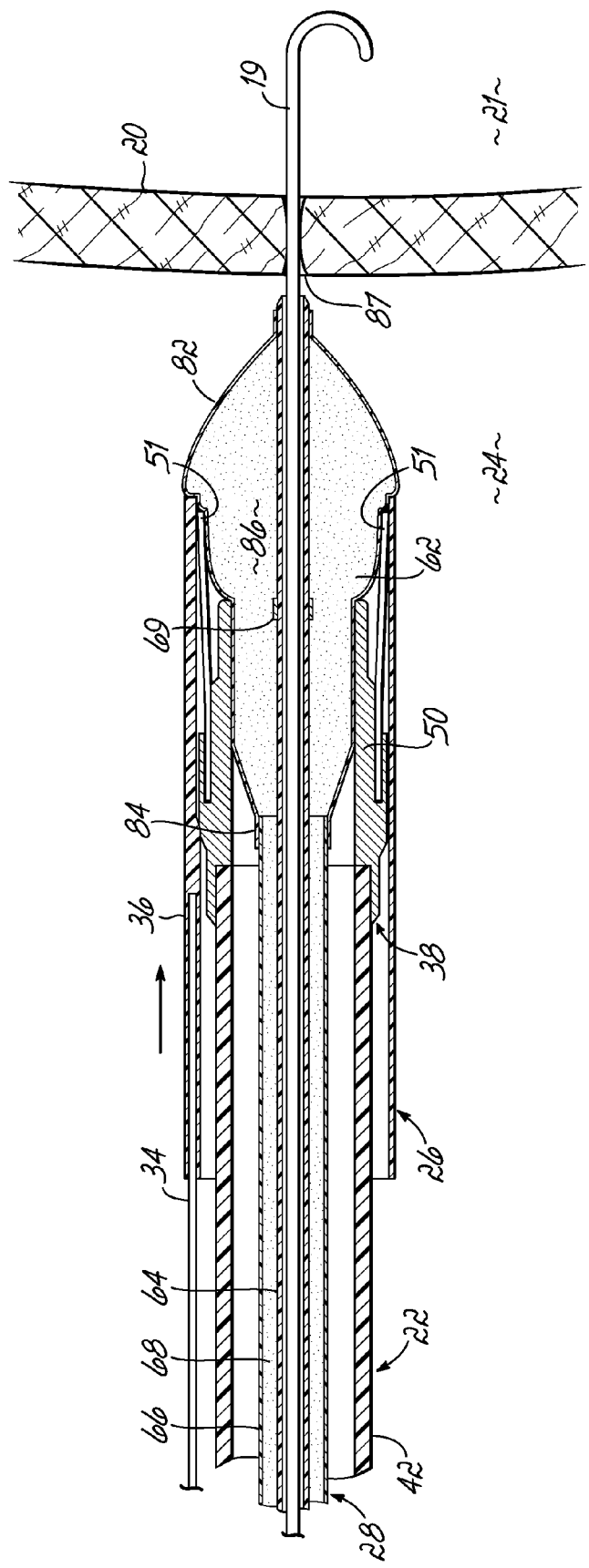

FIG. 4B illustrates the delivery apparatus 26, the transseptal cannula 22, and the coaxial balloon catheter 28 within the right atrium 24 and advanced to the intra-atrial septum 20.

Figure 4C:
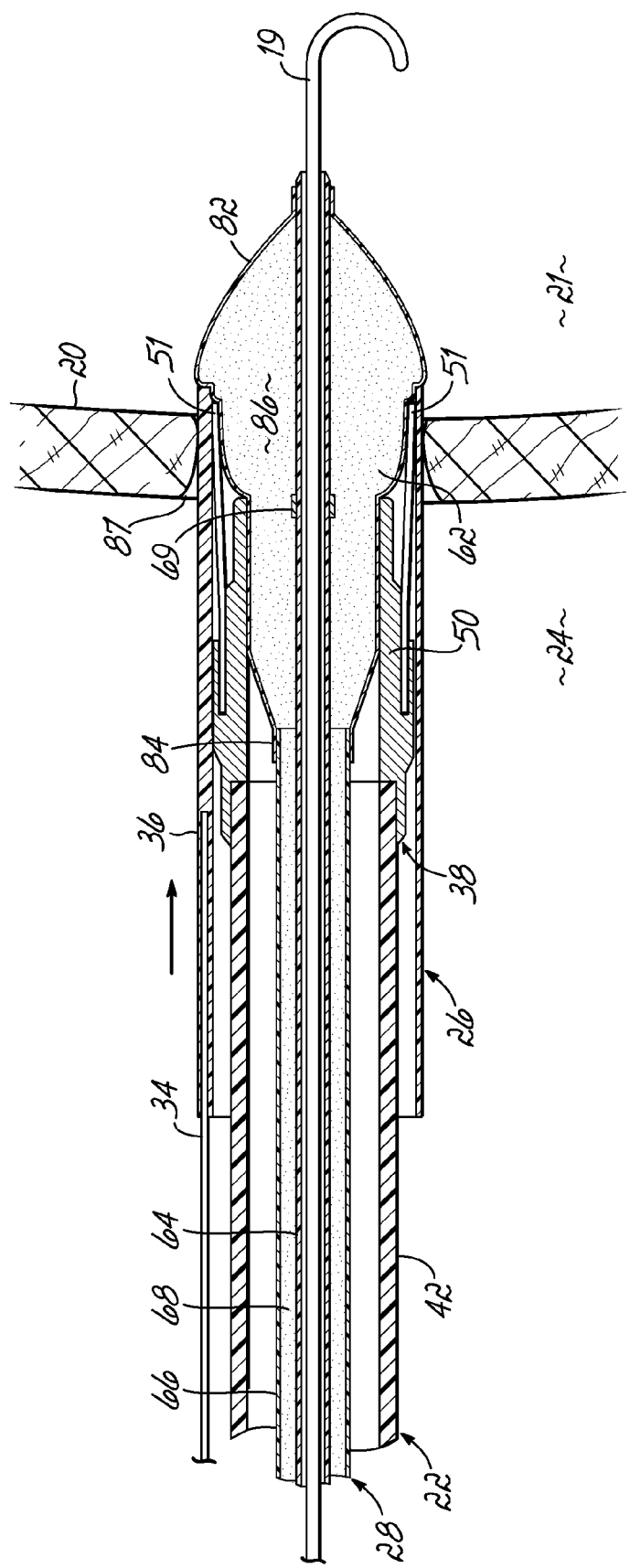

In FIG. 4C, the delivery apparatus 26 with the coaxial balloon catheter 28 and the transseptal cannula 22 are shown advancing, as a unit, through the intra-atrial septum 20 and into the left atrium 21. During the advancing, the distal cone structure 82 contacts and dilates the opening 87 through the intra-atrial septum 20 that was created previously by the guidewire 19. In this way, the opening 87 is sufficiently dilated so that the distal sleeve 36 may also easily enter the left atrium 21.

Figure 4D:
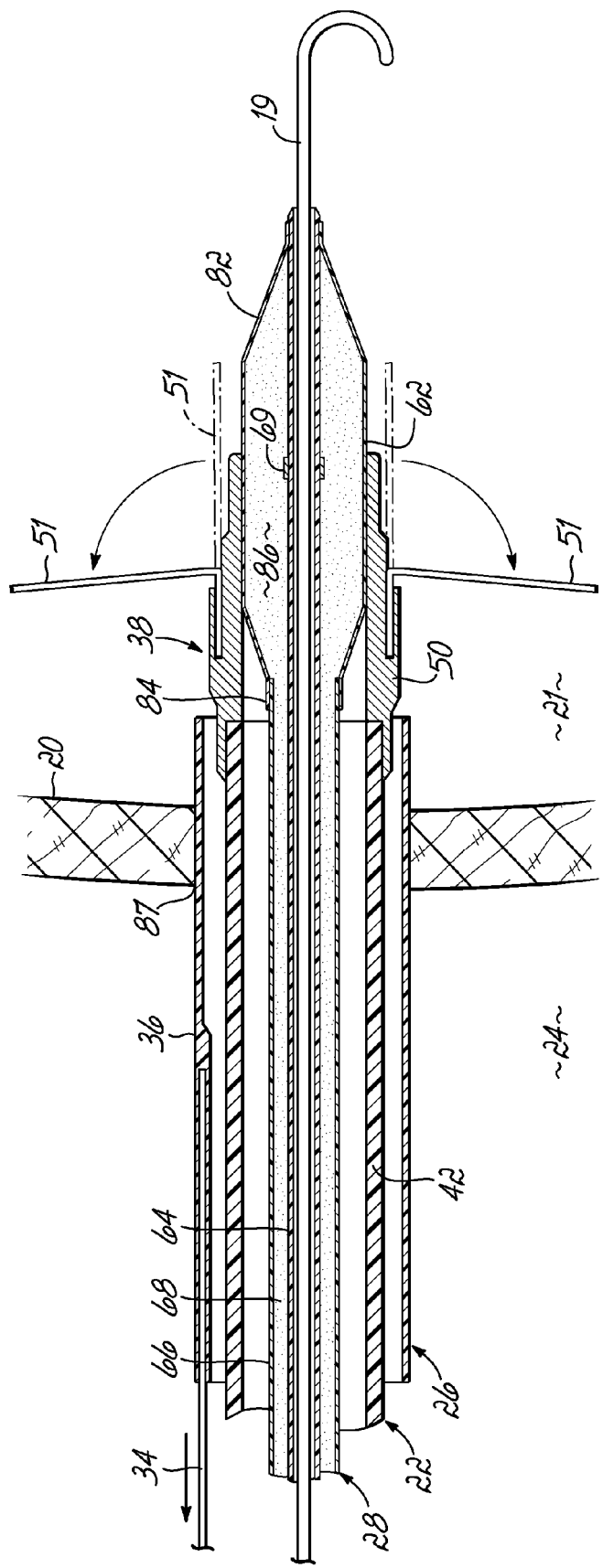

FIG. 4D illustrates one method of deploying the struts 51 of the left atrial anchor 38 within the left atrium 21 from a contracted state (shown in phantom) to an expanded state (shown in solid). Struts 51 in the expanded state are transverse to a lengthwise central axis of the flexible cannula body 42 and will resist movement of the transseptal cannula 22 in at least one direction along the lengthwise central axis. The struts 51 can be machined from a tubular structure, formed from wire, or formed from a flat sheet stock, which may be any superelastic, shape-memory material, such as nickel titanium (NiTi) or MP35N. In some embodiments, the struts 51 remain bare; however, it is possible to include a porous polymeric structure, such as a coating of calcium phosphate ($Ca_3(PO_4)_2$), collagen, or a porous polymeric fabric to promote tissue in-growth and further secure the tip 50 to the heart tissue.

Deploying the left atrial anchor 38 begins with the physician confirming that the tip 50 and the struts 51 are through the intra-atrial septum 20 and within the left atrium 21. The confirmation can be accomplished by in vivo localization of the marker 69 with X-ray, real-time fluoroscopy, or intracardiac echocardiograph. After the confirmation, the balloon 62 is at least partially deflated to remove the contact between the distal sleeve 36 and the balloon 62 such that the distal sleeve 36 moves with respect to the transseptal cannula 22 and the coaxial balloon catheter 28. However, the balloon 62 remains sufficiently inflated to maintain the contact between the tip 50 and the balloon 62. The coaxial balloon catheter 28 and the tip 50 are advanced, as a unit, further into the left atrium 21 while the distal sleeve 36 is held in position. In this way, the left atrial anchor 38 extends beyond the distal sleeve 36 of the delivery apparatus 26 and is deployed within the volume of the left atrium 21. The delivery apparatus 26 is then retracted from the left atrium 21, the intra-atrial septum 20, and the right atrium 24. Once deployed, struts 51 may have a diameter that is at least 1.1 times, but smaller than about 3 times, the diameter of the orifice created by the tip 50 through the intra-atrial septum 20; however, the diameter of the struts 51 in the expanded state is limited primarily by the patient's anatomy. Also, once deployed, the distal tip 50 can extend about 3 mm from the deployed left atrial anchor 38.

Figure 4E:
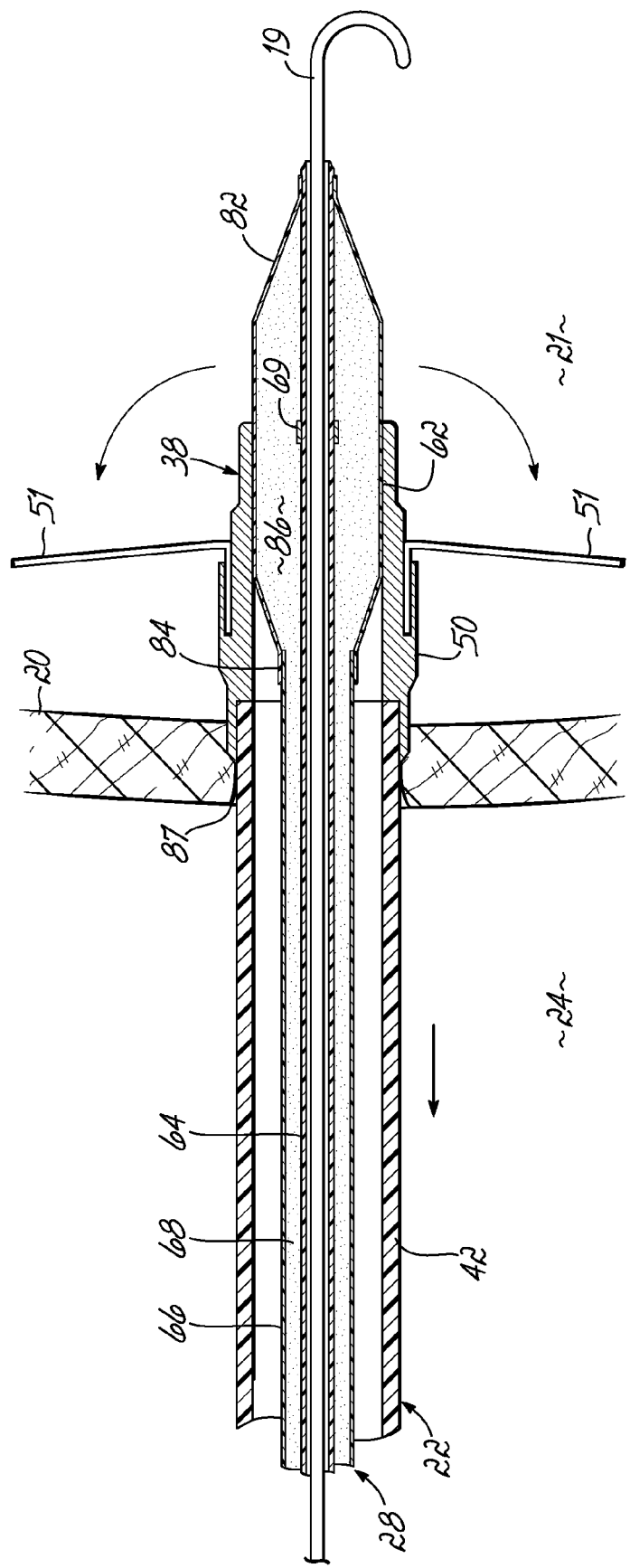

Continuing now to FIG. 4E, the physician can ensure proper deployment of the struts 51 by in vivo visualization of a radiopaque marker (not shown) on the struts 51. Once the struts 51 are fully deployed, the transseptal cannula 22 and the coaxial balloon catheter 28 are slightly retracted so that the struts 51 engage the intra-atrial septum 20 within the left atrium 21.

With the left atrial anchor 38 deployed at the intra-atrial septum 20, a right atrial anchor 88 can be implanted, which will now be described in detail with reference to FIGS. 5A-5B.

Figure 5A:
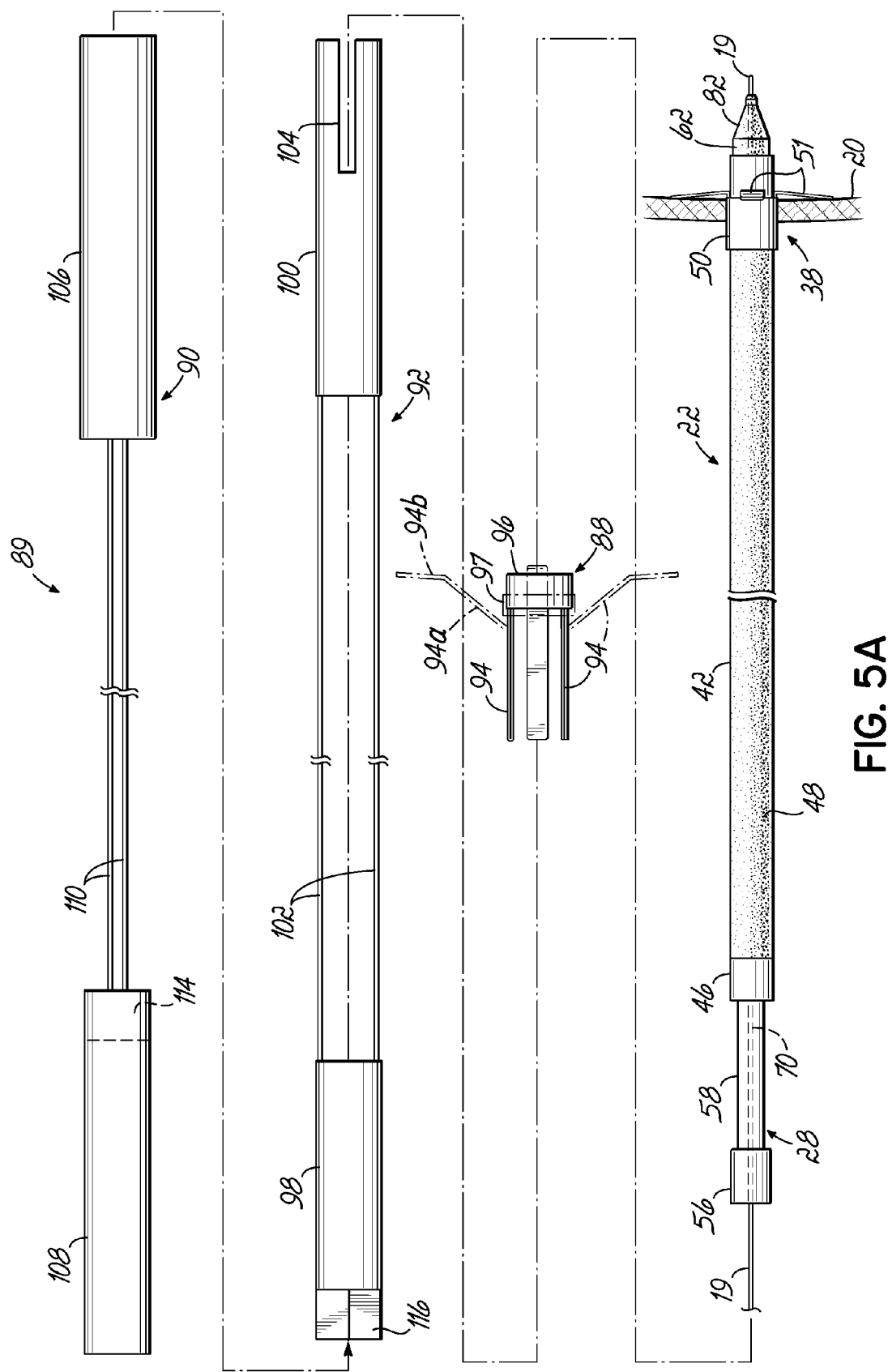
FIG. 5A is a disassembled, side elevational view of a right atrial anchor delivery system with the transseptal cannula and the coaxial balloon catheter.

FIG. 5A illustrates the details of the right atrial anchor 88 and a right atrial anchor delivery system 89. The right atrial anchor 88 has at least two opposed struts 94 coupled to a tip 96, where the struts 94 are operable to move from a contracted state (shown in solid) to an extended state (shown in phantom). The struts 94 may be machined from a tubular structure formed using wire or formed from a flat sheet stock, as was described in U.S. patent application Ser. No. 12/256,911. The wire or flat sheet stock may be any shape-memory material (such as nickel titanium, NiTi, or MP35N). While many shapes for the struts 94 are possible, the shape shown includes an angled portion 94a and a contact portion 94b in the extended state. The contact portion 94b will contact the intra-atrial septum 20 (FIG. 1). The angled portion 94a allows the right atrial anchor 88 to accommodate a wide range of anatomies and septal wall thicknesses. The angled portion 94a also creates a force that will resist a distal movement of the transseptal cannula 22 once the right atrial anchor 88 is properly attached to the left atrial anchor 38 and implanted in the intra-atrial septum 20 (FIG. 1).

The tip 96 can be constructed in a manner that is similar to that described previously with respect to the tip 50 of the left atrial anchor 38.

In some embodiments, the right atrial anchor 88 can include an anchor cuff 97 (shown in phantom) to promote localized tissue growth. The anchor cuff 97 can be a porous polymeric structure constructed from an implantable porous material (e.g., ePTFE, DACRON) as an inner cuff (not shown) and/or an outer cuff 97 similar to that described previously with the left atrial anchor 38. In other embodiments, such as those provided in U.S. patent application Ser. No. 12/256,911, the right atrial anchor 88 may include a full disc (not shown) surrounding all of the struts 94. The full disc can also be constructed from an implantable porous material (e.g., ePTFE, DACRON). While a separate full disc (not shown) could also surround all of the struts 51 of the left atrial anchor 38, the configuration surrounding the struts 94 of the right atrial anchor 88 is preferred because the right atrium 24 is larger in volume than the left atrium 21.

FIG. 5A further illustrates the right anchor delivery apparatus 92 used to deliver the right atrial anchor 88 to the intra-atrial septum 20 (FIG. 1). The right anchor delivery apparatus 92 has a proximal hub 98 and a distal sleeve 100 connected to the proximal hub 98 by at least one connector member 102 (two connector members 102 are shown). The proximal hub 98, which can be molded from a single polymeric material, provides visual and tactile feedback to the physician throughout the surgical procedure. The connector members 102 are made of a single polymeric or metallic material and should be constructed with a low profile. The low profile allows the physician to maintain greater control over the transseptal cannula 22 while manipulating the right anchor delivery apparatus 92. The distal sleeve 100 holds the right atrial anchor 88 during delivery to the transseptal cannula 22 and the intra-atrial septum 20 (FIG. 1). In some embodiments, the distal sleeve 100 includes notches 104 into which the struts 94 of the right atrial anchor 88 rest. The notches 104 also contribute to an over-all low-profile assembly. The number of notches 104 should equal the number of struts 94 of the right atrial anchor 88.

FIG. 5A also illustrates the right anchor sheath 90. The right anchor sheath 90 includes a distal sleeve 106 and a proximal hub 108 and sheath body configured to receive and move relative to the right anchor delivery apparatus 92. The sheath body, as illustrated, includes a distal sleeve 106 that is connected to the proximal hub 108 by at least one connector member 110 (two connector members are shown). The distal sleeve 106 secures the struts 94 of the right atrial anchor 88 in a contracted state. The distal sleeve 106 may be constructed from single polymeric or multiple polymeric layers. The length of the distal sleeve 106 should cover the length of the struts 94 in the contracted state.

The proximal hub 108 provides the physician with visual and tactile feedback when the distal sleeve 106 is moved relative to the transseptal cannula 22. The proximal hub 108 is typically molded from a single polymeric material and has sufficient rigidity so as to not be damaged or deformed during normal handling by the physician. The connector members 110 are constructed from a rigid polymeric material or metallic structure, such as a wire, and surround the transseptal cannula 22. This arrangement creates a low profile and allows the physician to maintain direct control of the transseptal cannula 22 while manipulating the distal sleeve 106.

As was previously described with the delivery apparatus 26 (FIG. 2), used to deploy the left atrial anchor 38 (FIG. 2), the right anchor sheath 90 may alternatively include a sheath extending from the proximal hub and for the length of the right anchor delivery apparatus 92. The sheath is directed over the right anchor delivery apparatus 92 and secures the right atrial anchor 88 until deployment.

Figure 5B:
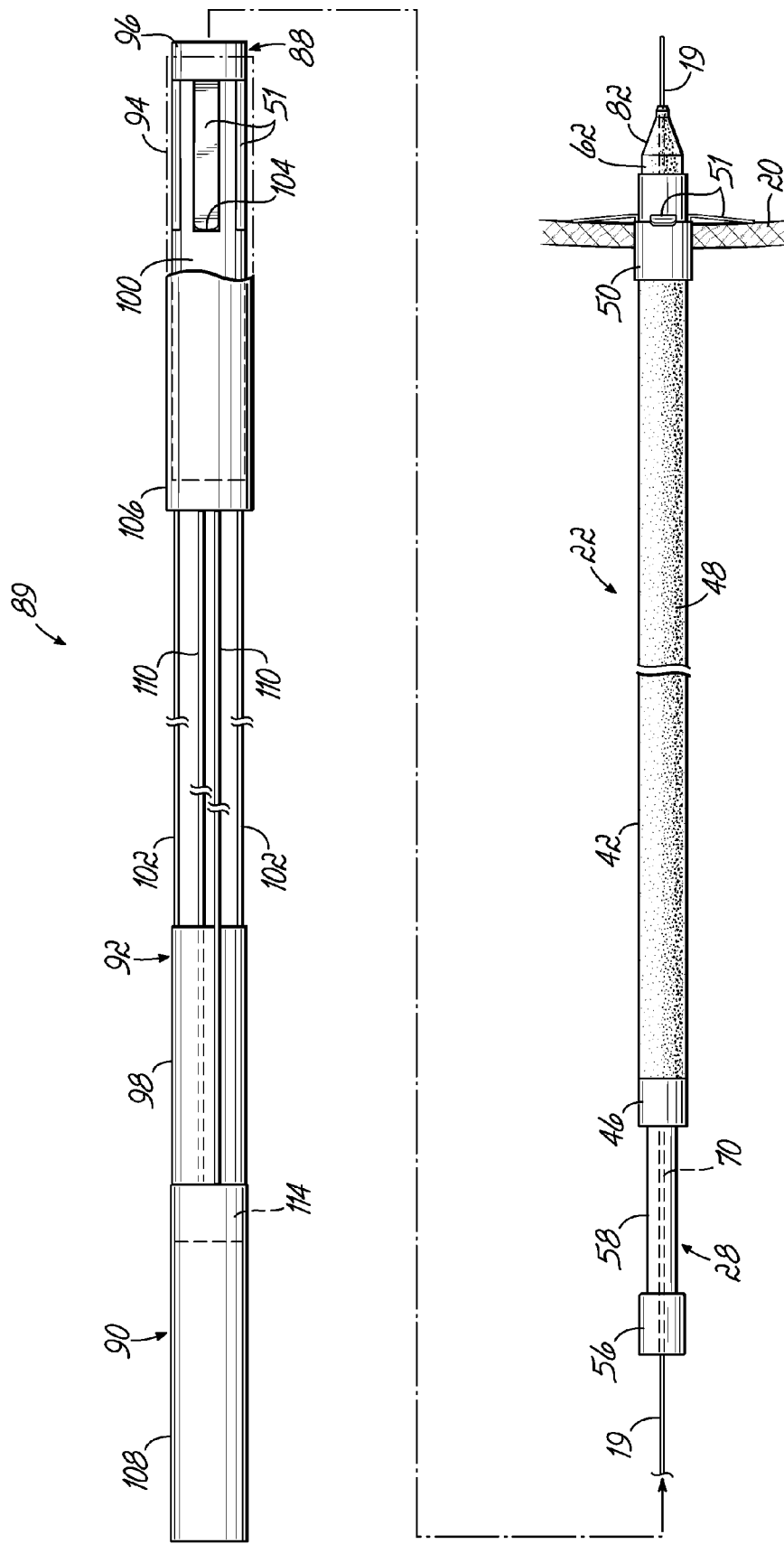
FIG. 5B is an assembled, side elevational view of the right atrial anchor delivery system with the transseptal cannula and coaxial balloon catheter.

FIG. 5B illustrates the assembled right anchor delivery system 89, including the right anchor sheath 90 and the right anchor delivery apparatus 92 with the right atrial anchor 88. The right anchor delivery system 89 is back-loaded over the guidewire 19, the coaxial balloon catheter 28, and the transseptal cannula 22.

With the details of the right anchor delivery system 89 described with some detail, the method of implanting the right atrial anchor 88 can continue with reference to FIGS. 6A-6J.

Figure 6B:
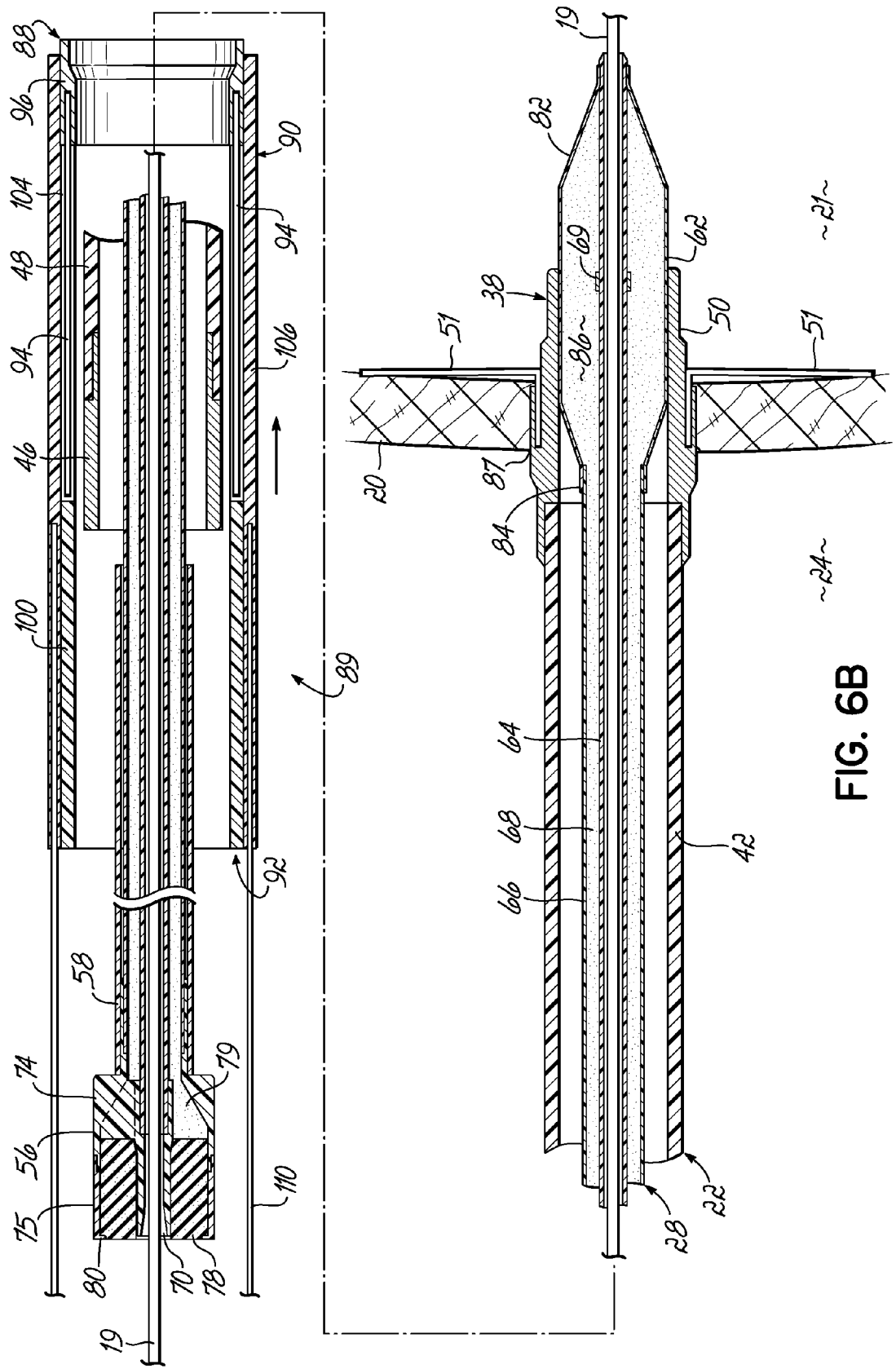
FIG. 6B is a side elevation view in partial cross-section of the exemplary method of back-loading the right anchor delivery system over the transseptal cannula assembly.

FIGS. 6A-6B illustrate the method of assembling the right anchor delivery system 89, and the loading of the right anchor delivery system 89 over the coaxial balloon catheter 28 and the transseptal cannula 22. As shown, the proximal hubs 108, 98 may each include an alignment member 114, 116, respectively. The alignment members 114, 116 maintain a radial alignment between the right anchor delivery apparatus 92 and the right anchor sheath 90 during the delivery of the right atrial anchor 88. The alignment members 114, 116 can be molded as a portion of the respective proximal hubs 108, 98. As also shown, the alignment members 114, 116 have similar perimeter shape; however, the alignment member 114 is formed as a negative image of the alignment member 116. This structure allows the alignment member 114, 116 to mate and resist rotational movement. However, the particular shapes and arrangements shown should not be considered limiting.

Figure 6C:
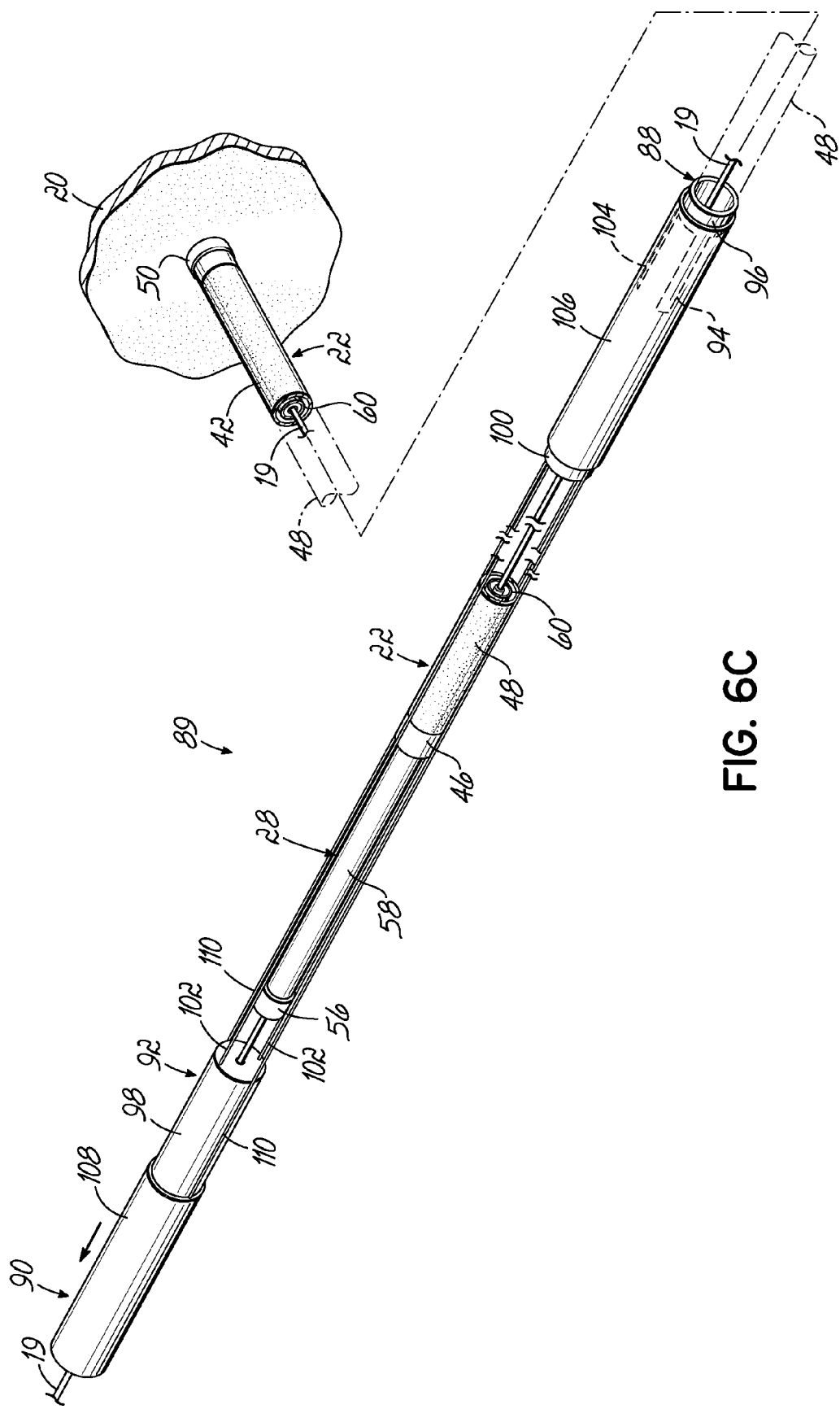
FIG. 6C is a perspective view of an exemplary method of advancing the right anchor delivery system over the transseptal cannula assembly.

FIG. 6C illustrates the assembled right anchor delivery apparatus 92 and the loading of the right anchor delivery apparatus 92 and the right anchor sheath 90, as a unit, over the right anchor delivery system 89 to the intra-atrial septum 20.

Figure 6D:
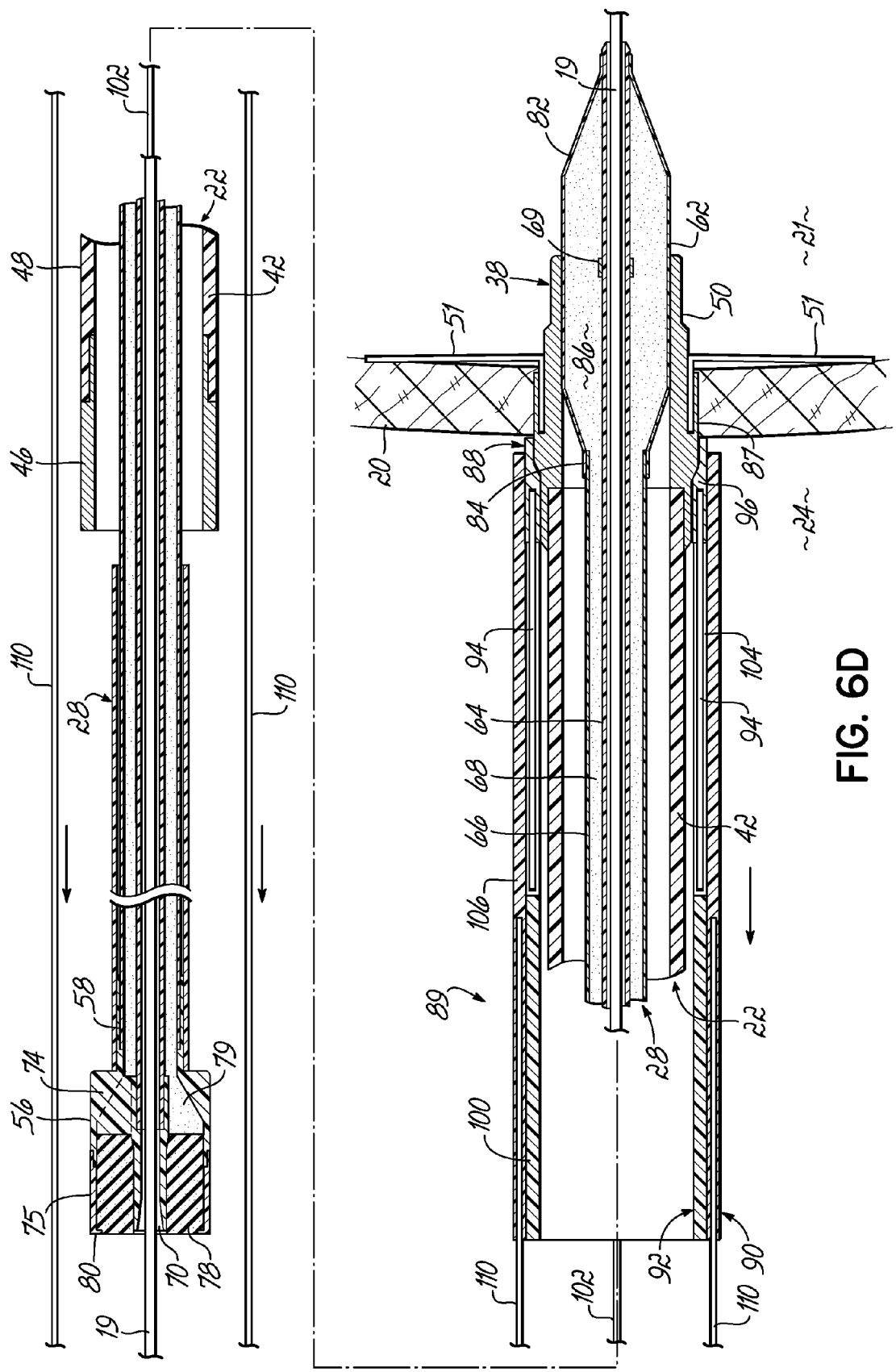
FIG. 6D-6E are side elevation views in cross section of an exemplary method of deploying the right atrial anchor of the transseptal cannula assembly.

FIG. 6D illustrates the right atrial anchor 88 positioned at the intra-atrial septum 20. The right atrial anchor 88 may now be attached to the tip 50 by way of a mechanical connection, such as a friction or interference fit, a magnet, or a screw thread. The struts 94 are then deployed, as described below.

Figure 6E:
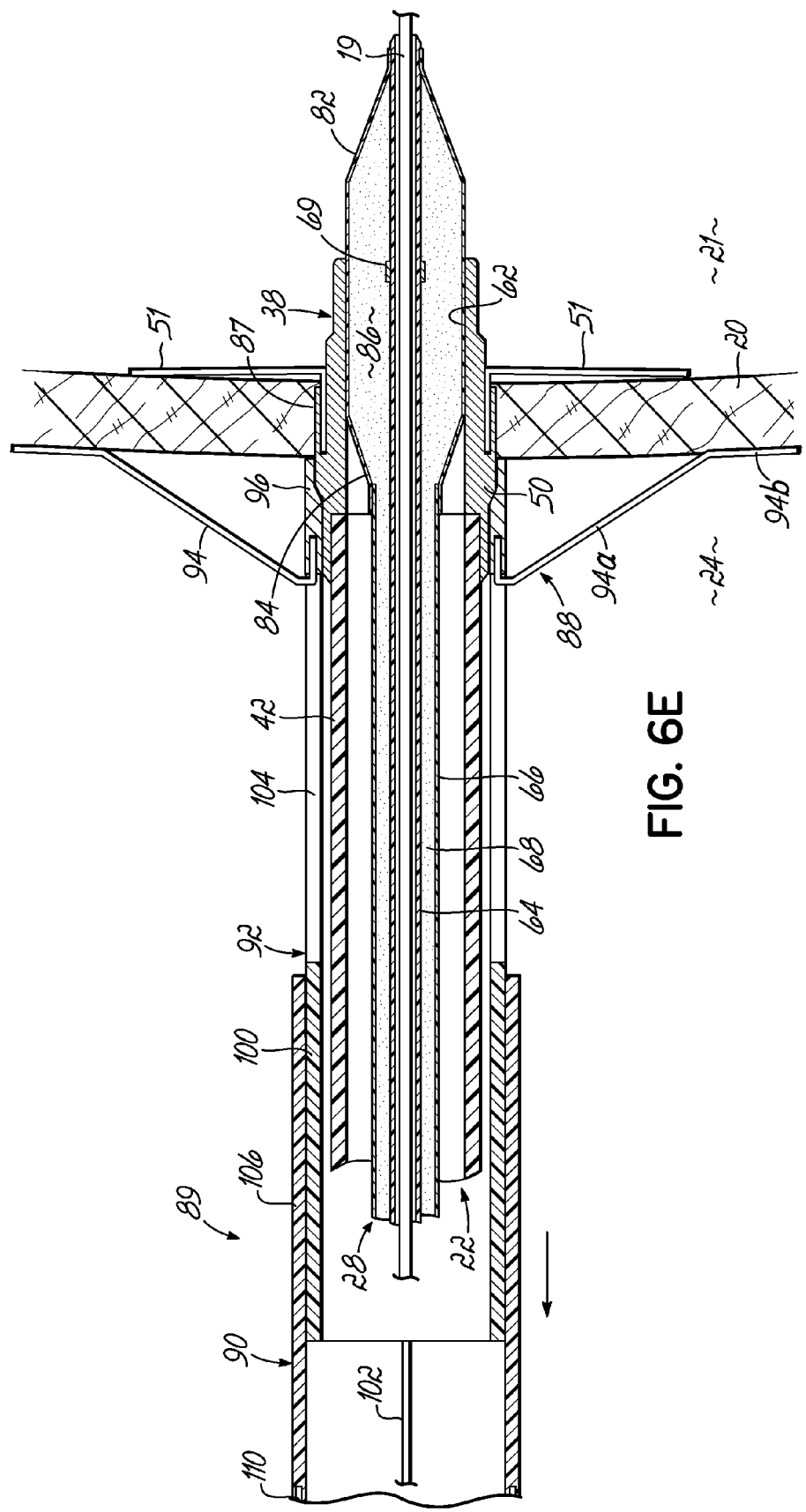

FIG. 6E illustrates the right anchor delivery apparatus 92 positioned against the intra-atrial septum 20 as the distal sleeve 106 is retracted. After sufficient retraction, the struts 94 are released to automatically deploy from the contracted state (shown in solid in FIG. 6D) to a deployed state (shown in solid) against the intra-atrial septum 20.

FIG. 6F illustrates the right atrial anchor 88 having at least one locking member 118 on the inner diameter of the tip 96. The at least one locking member 118 provides one manner of attaching and securing the tip 96 of the right atrial anchor 88 to the tip 50 (FIG. 6E) of the left atrial anchor 38 (FIG. 6E). The locking members 118 can include any manner of creating and maintaining a compression fit between the tip 96 of the right atrial anchor 88 and the tip 50 of the left atrial anchor 38.

Figure 6G:
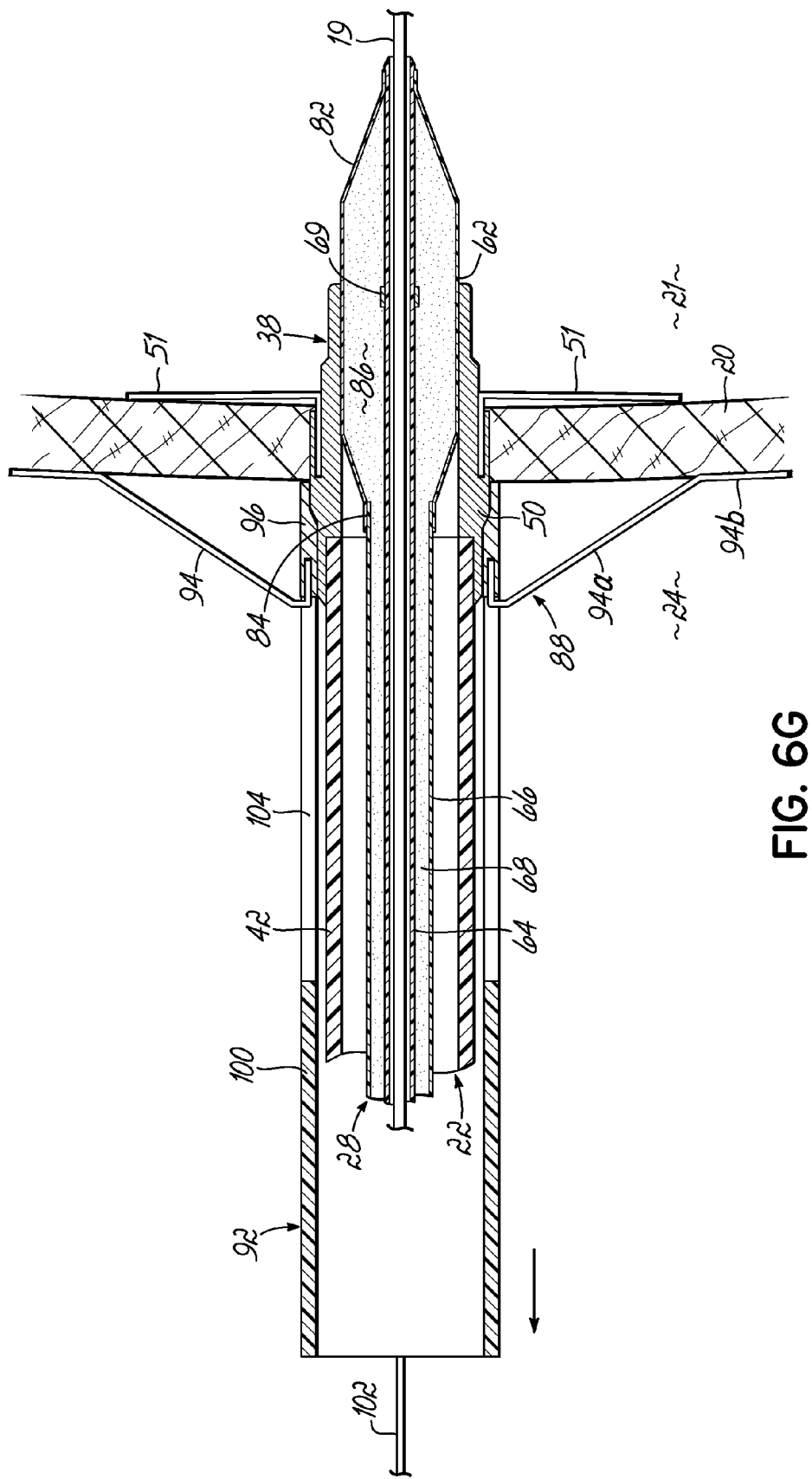
FIGS. 6G-6J are side elevational views in cross section of the exemplary method of completing the implanting of the right atrial anchor of the transseptal cannula assembly.

FIG. 6G illustrates the retraction of the right anchor delivery apparatus 92 once the tip 96 of the right atrial anchor 88 is secured and the struts 94 are deployed.

Figure 6H:
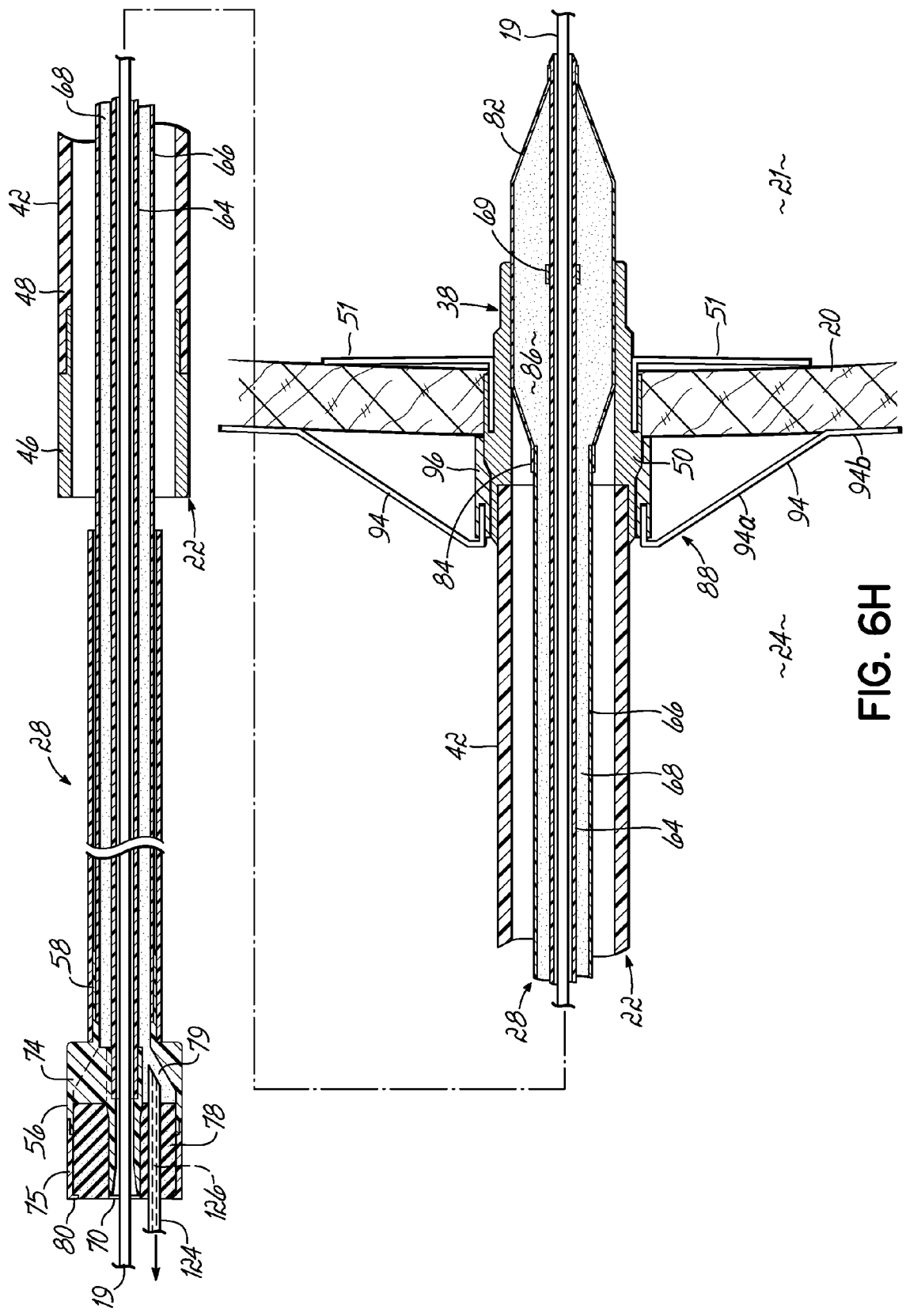

FIG. 6H then illustrates the deflating of the coaxial balloon catheter 28. The syringe needle 124 of the syringe is inserted through the grommet 78 and into the fluid space 79 of the coaxial hub 56. The inflation fluid is then withdrawn through the lumen 126 of the syringe needle 124 and into the syringe, which will decrease the fluid pressure within the balloon 62 and cause deflation.

Figure 6I:
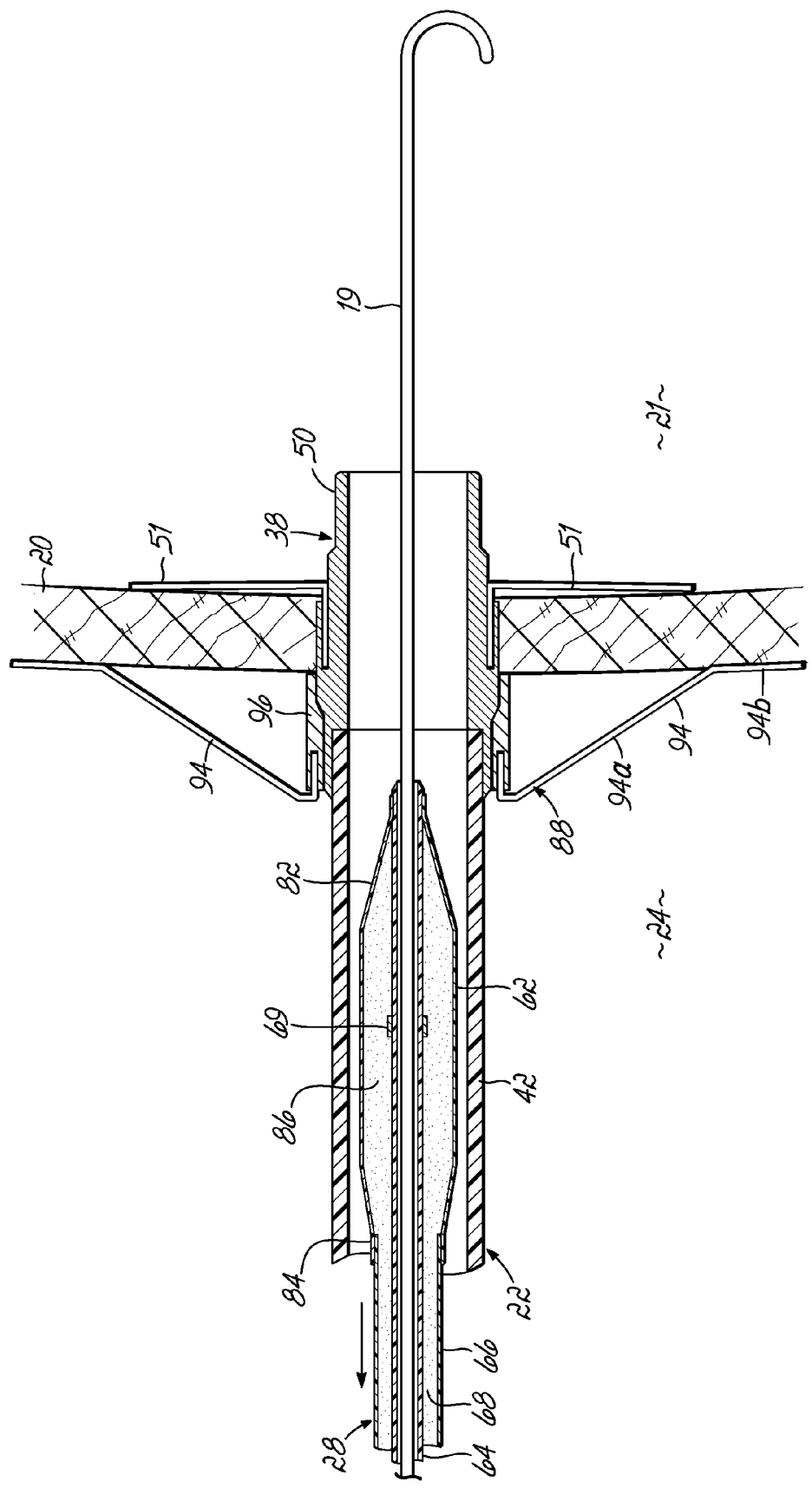
Figure 6J:
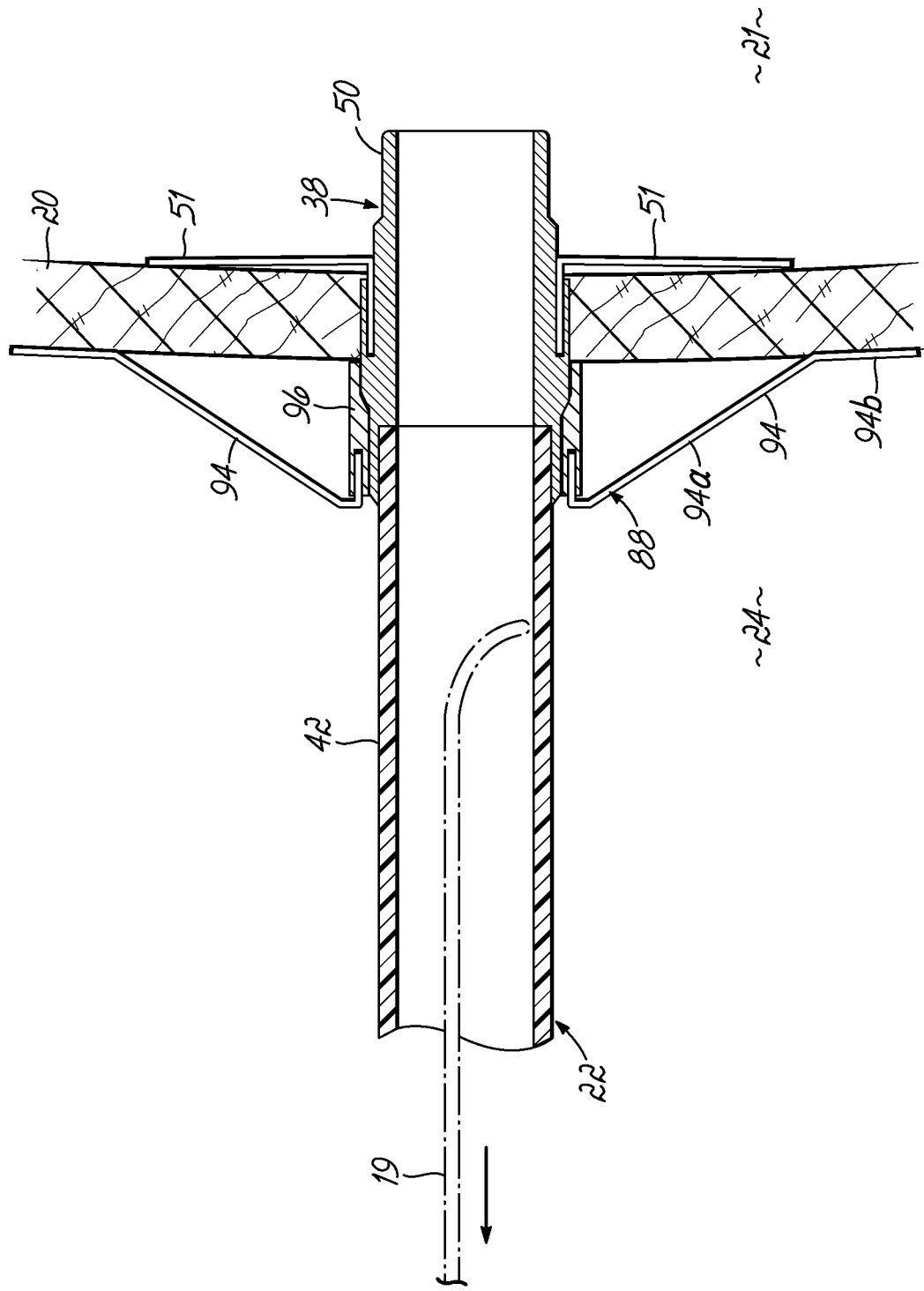

After sufficient deflation, as shown in FIG. 6I, the balloon 62 is released from its contact with the inner surface of the tip 50 and can be retracted. The coaxial balloon catheter 28 is then retracted, followed by the guidewire 19 shown in FIG. 6J.

Though not specifically shown, after the guidewire 19 is removed it would be permissible for the physician to attach a hemostasis cuff (not shown) where the proximal end of the transseptal cannula 22 meets the incision into the right subclavian vein 15 and before attaching the transseptal cannula 22 to the pump of the circulatory assist device, and as disclosed in U.S. patent application Ser. No. 12/256,911. The hemostasis cuff seals the incision into the right subclavian vein 15 and may provide further resistance to movement of the transseptal cannula 22.

Figure 6K:
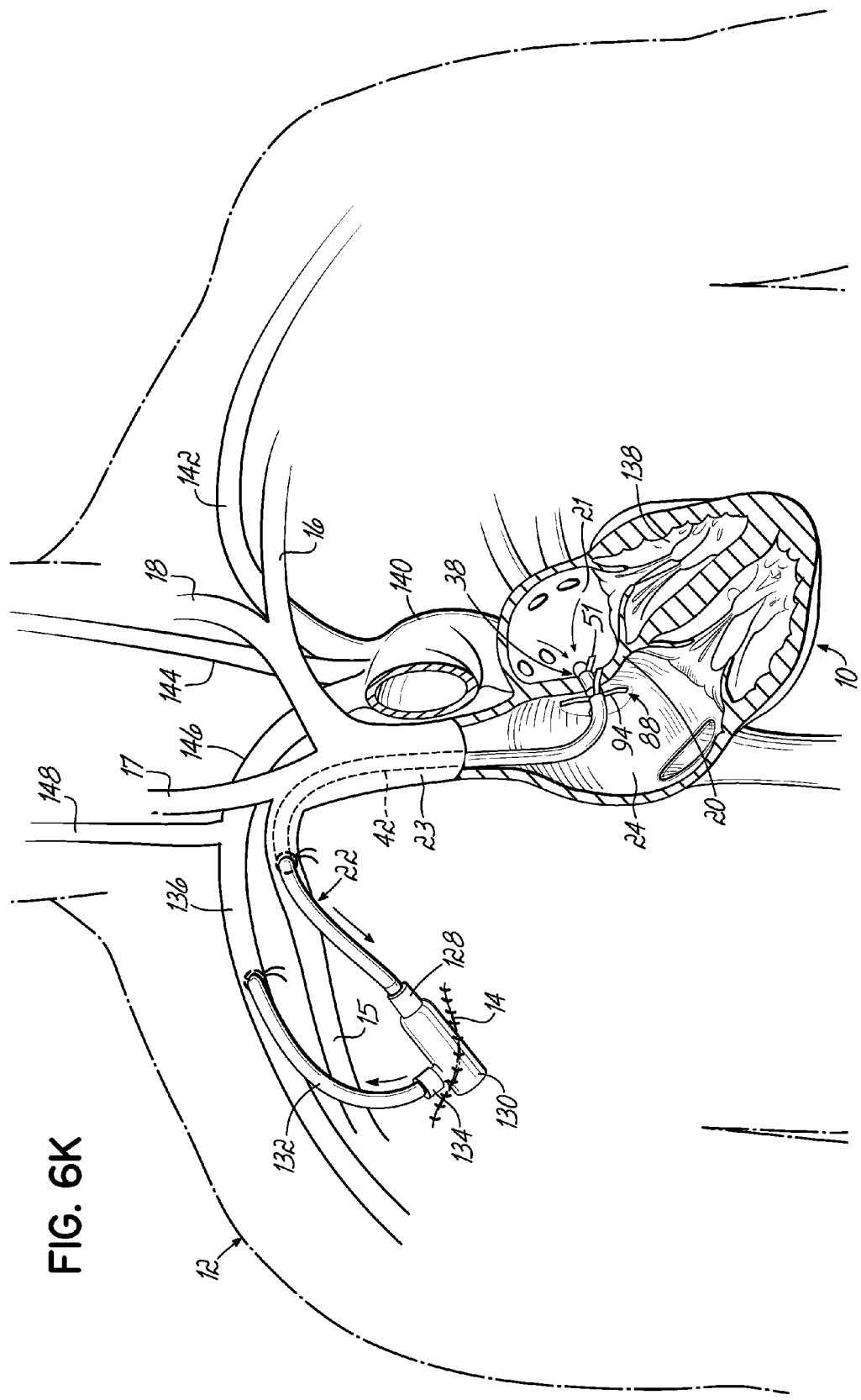
FIG. 6K is a diagrammatic view of an illustrative circulatory assist system positioned in the human heart, shown in cross-section.

Finally, FIG. 6K illustrates the implanted circulatory assist system. In that regard, the transseptal cannula 22, which extends from the right and left atrial anchors 88, 38 to the superior incision site 14, is attached to an inflow port 128 of an implantable pump 130 of the circulatory assist device. An outflow cannula 132 is coupled to the outflow port 134 of the pump 130. The opposing end of the outflow cannula 132 is surgically attached as so to communicate with a suitable superficial artery, such as the right subclavian artery 136. At this time, the physician may position the pump 130 subcutaneously or submuscularly within the superior incision site 14 or maintain the pump 130 externally even after the superior incision site 14 is closed.

While not specifically shown, the pump 130 can be operably associated with a controller (not shown), which may also be implanted or remain external to the patient 12. A signal transmission means (not shown) is provided between the pump 130 and the controller and may be either a hard-wired or wireless communications device. In operation, the controller may regulate the pumping action of the pump 130. Additionally, a memory device (not shown) may be included within the controller that will record pump activity for subsequent doctor evaluation and interaction.

The completed flow of blood according to a preferred embodiment will be as follows: oxygenated blood will exit the left atrium 21 via the natural path, into the left ventricle 138, to the aorta 140. From the aorta 140, blood moves into the left subclavian artery 142, the left common carotid artery 144, and the brachiocephalic trunk 146, which supplies oxygenated blood to the right common carotid 148 and the right subclavian artery 136. Oxygenated blood will also enter the transseptal cannula 22 from the left atrium 21. Blood entering the flexible cannula body 42 of the transseptal cannula 22 will travel through the lumen of the flexible cannula body 42 to the pump 130. The pump 130 actively pumps blood into the outflow cannula 132 and into the right subclavian artery 136. From here, the blood is directed into the remainder of the vascular network.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A coaxial balloon catheter comprising:
   a tube body including an inner member and an outer member surrounding the inner member and thereby creating an inflation channel between the inner and outer members;
   a coaxial hub coupled to a proximal portion of the tube body and including a fluid space in fluid communication with the inflation channel and further including a guidewire lumen, the coaxial hub having a low profile so that a surgical device can be loaded over the coaxial hub, the hub further including an annular grommet surrounding the guidewire lumen, and with a central aperture of the annular grommet aligned with the guidewire lumen, the grommet providing a fluidtight seal for the inflation channel and being puncturable to permit an inflation needle to pass therethrough for communication with the fluid space; and
   a balloon coupled to a distal portion of the tube body, wherein a distal portion of the inner member extends through the balloon thereby creating an annular cavity between a wall of the balloon and the inner member.

2. The coaxial balloon catheter of claim 1, wherein the inner member within the balloon further includes a radiopaque marker.

3. The coaxial balloon catheter of claim 1, wherein the balloon further includes a distal cone structure operable to dilate an opening within a heart tissue.

4. The coaxial balloon catheter of claim 1, wherein the coaxial hub further includes a hub-body coupled to a hub-cap and enclosing the grommet.

5. The coaxial balloon catheter of claim 4, wherein the coaxial hub further includes a plurality of spokes positioned adjacent the grommet.

6. The coaxial balloon catheter of claim 5, wherein the plurality of spokes is operable to couple the inner member to the coaxial hub.

7. The coaxial balloon catheter of claim 5, wherein the plurality of spokes is operable to provide a positive stop for the grommet.

8. The coaxial balloon catheter of claim 4, wherein the hub-cap further includes a grommet retention feature operable to prevent migration of the grommet.

* * * * *